United States Patent [19]

Furmaniak-Wehr

[11] Patent Number: 5,705,400
[45] Date of Patent: Jan. 6, 1998

[54] ASSAY FOR ADRENAL AUTOANTIGEN

[75] Inventor: Jadwiga Maria Furmaniak-Wehr, Cardiff, United Kingdom

[73] Assignee: RSR Limited, Cardiff, United Kingdom

[21] Appl. No.: 115,052

[22] Filed: Sep. 2, 1993

Related U.S. Application Data

[63] Continuation-in-part of Ser. No. 937,409, Aug. 31, 1992, abandoned.

[30] Foreign Application Priority Data

| Mar. 7, 1992 | [GB] | United Kingdom | 9205040 |
| Jul. 31, 1992 | [GB] | United Kingdom | 9216306 |
| Apr. 24, 1993 | [GB] | United Kingdom | 9308544 |

[51] Int. Cl.$^6$ .................. G01N 33/564; G01N 33/567; G01N 33/573

[52] U.S. Cl. .................. 436/506; 435/7.1; 435/7.4; 435/7.92; 435/7.95; 435/18; 435/195; 436/811; 436/503

[58] Field of Search ................. 435/7.9, 7.92, 435/7.93, 7.94, 7.95, 18, 7.1, 7.4, 195; 436/506, 811, 503

[56] References Cited

U.S. PATENT DOCUMENTS

| 3,654,090 | 4/1972 | Schuurs et al. | 435/7.93 |
| 4,720,454 | 1/1988 | White et al. | 435/6 |
| 5,070,192 | 12/1991 | Earnshaw et al. | 536/27 |
| 5,254,458 | 10/1993 | Mimms | 435/5 |
| 5,376,533 | 12/1994 | Maclaren et al. | 435/7.4 |

FOREIGN PATENT DOCUMENTS

| 0 094 603 | 5/1983 | European Pat. Off. |
| 340 878 | 11/1989 | European Pat. Off. |
| 360 361 | 3/1990 | European Pat. Off. |
| WO 91/02061 | 2/1991 | WIPO |

OTHER PUBLICATIONS

Bednarek, J. et al. Steroid 21–Hydroxylase is a Major Autoantigen Involved in Adult Onset Auto–Immune Addison's Disease. FEBS Letters 309:51–55, 1992.

Wedlock, N. et al. Autoimmune Addison's Disease: Analysis of Autoantibody Binding Sites on Human Steroid 21–Hydroxylase. FEBS Letters 332:123–126, 1993.

Bumpus, JA et al. Bovine Adrenocortical Microsomal Hemeproteins p. 450 17α and p. 450 c–21. J. Biol. Chem. 257:12696–704, 1982.

Alberts, B et al, Molecular Biology of the Cell. New York: Garland Publishing, 1989. pp. 169–174 & 262–267.

Khoury, et al., "Surface–Reactive Antibodies to Human Adrenal Cells in Addison's Disease," Clin. exp. Immunol., 1981, 45:48–55.

Scherbaum, et al., "Development of Adrenocortical Failure in Non–Addisonian Patients with Antibodies to Adrenal Cortex," 1982, 16:345–352.

Kosowicz, et al., "A Radioimmunoassay for the Detection of Adrenal Autoantibodies," Clin. exp. Immunol., 1986, 63:671–679.

Betterle, et al., "The Natural History of Adrenal Function in Autoimmune Patients With Adrenal Autoantibodies," J. Endocr., 1988, 117:467–475.

Freeman, et al., "T and B Cell Reactivity to Adrenal Antigens in Autoimmune Addison's Disease," Clin. exp. Immunol., 1992, 88:275–279.

(List continued on next page.)

Primary Examiner—Paula K. Hutzell
Assistant Examiner—James L. Grun
Attorney, Agent, or Firm—Baker & Botts, L.L.P.

[57] ABSTRACT

Adrenal autoantigen is isolated and characterised as a protein obtainable from the microsome fraction of the adrenal gland, having a molecular weight of about 55,000 and antigenic towards adrenal autoantibody. The protein is used in a method for detecting adrenal autoantibodies.

1 Claim, 12 Drawing Sheets

OTHER PUBLICATIONS

Bright, et al., "Adrenal Autoantibodies Bind to Adrenal Subcellular Fractions Enriched in Cytochrome-c Reductase and 5'-Nucleotidase", J. Clin. Endo. Meta., 70:95-99 (1990).

Centeno, et al., "Isolation and Characterization of a Rabbit Adrenal Autoantigen", Immunology, 24:901-910 (1973).

Chouinard, et al., "ACTH-induced Increases in Rabbit Adrenal Immunoreactive $P-450_{17a}$ and $P-450_{21}$", Mol. and Cell. Endocrinology, 68:29-34 (1990).

Furmaniak et al., "Immunoprecipitation of Human Adrenal Microsomal Antigen," FEB, 231:25-28 (1988).

King et al., "Control of Yeast Mating Signal Transduction by a Mammalian $\beta_2$-Adrenergic Receptor and $G_{-s}$ $\alpha$ Subunit", Science, 250:121-125 (1990).

Krohn et al., "Identification by Molecular Cloning of an Autoantigen Associated with Addison's Disease as Steroid 17α-Hydroxylase," The Lancet, 339:770-773 (1992).

White et al., "Cloning and Expression of cDNA Encoding a Bovine Adrenal Cytochrome P-450 Specific for Steroid 21-Hydroxylation," Proc. Natl. Acad. Sci., 81:1986-1990 (1984).

White et al., "Structure of Human Steroid 21-Hydroxylase Genes", Proc. Natl. Acad. Sci., 83:5111-5115 (1986).

Wingvist et al., "21-Hydroxylase, A Major Autoantigen in Idiopathic Addison's Disesase," The Lancet, 339:1559-1562 (1992).

Editorials, The Lancet, 339:779-780 (1992).

Gosling, "A Decade of Development in Immunoassay Methodology", Clin. Chem., 36(8):1408-1427 (1990).

ASSAY FOR ADRENAL AUTOANTIGEN

This application is a continuation-in-part application of U.S. Ser. No. 07/937,409 filed Aug. 31, 1992, now abandoned.

BACKGROUND OF THE INVENTION 1. Field of the Invention

The present invention relates to adrenal autoantigen. More particularly, it relates to immunoassays for adrenal autoantibodies involving adrenal autoantigen. The invention further relates to methods of using adrenal autoantigen in the diagnosis of autoimmune Addison's disease. 2. Brief Description of the Related Art Addison's disease is a disorder characterised by failure of the adrenal gland and is often an autoimmune disorder involving destruction of the adrenal cortex and the presence of adrenal autoantibodies in the patient's serum. The adrenal cortex is responsible for producing several steroid hormones including cortisol, aldosterone and testosterone. In autoimmune Addison's disease and other forms of the disease, levels of these hormones are reduced. This reduction in hormone levels is responsible for the clinical symptoms of the disease which include low blood pressure, muscle weakness, increased skin pigmentation and electrolyte imbalance.

Autoantibodies to the adrenal cortex were first described in 1957 using the technique of complement fixation[1]. Subsequently other laboratories confirmed the presence of these autoantibodies using complement fixation or immunofluorescence[2-4]. Radioimmunoassay and ELISA techniques have also been described using crude adrenal membrane preparations[5-6].

The preparation of purified rabbit adrenal autoantigen was reported in 1973[7] but the isolation of human adrenal autoantigen remained an elusive goal. The human adrenal autoantigen(s) has/have been localised to the microsomal fraction of adrenal tissue homogenates and in 1988 it was shown that the antigen is a membrane protein with a molecular weight of about 55,000[11]. In 1990 there was described an assay to detect binding of adrenal autoantibodies to subcellular fractions of the human adrenal gland[8]. The assay indicated that the autoantibody has a plasma membrane and/or microsomal source and was described as providing a more rational approach to "eventual" antigen isolation and purification.

Measurement of adrenal autoantibodies is important in the diagnosis of Addison's disease and currently immunofluorescence is used routinely.

SUMMARY OF THE INVENTION

The present inventor has for the first time succeeded in isolating and characterising an adrenal antigen. The isolation and characterisation of the antigen enables the production of the antigen, for example, by recombinant techniques, the generation of antibodies to the antigen, purification of adrenal autoantibody and assays for the antigen. Such assays are useful for the diagnosis of latent or actual autoimmune Addison's disease.

The present invention relates to assays for adrenal autoantibodies. Preferred assays of the invention involve the use of a protein obtainable from the microsome fraction of human or animal adrenal glands. The protein has an observed molecular weight of approximately 50,000 to 60,000 and is antigenic towards adrenal autoantibody. Preferably the protein is of human origin.

The invention further relates to assays involving the use of protein comprising an epitope for adrenal autoantibody, having an observed molecular weight of from about 50,000 to about 60,000 and obtainable by:

homogenising adrenal glands, subjecting the homogenate to differential centrifugation to obtain a microsome fraction, suspending the microsome fraction in a phosphate buffer, centrifuging the suspension in the presence of sodium cholate to form a supernatant, adding polyethylene glycol and further sodium cholate to the supernatant and mixing the supernatant, centrifuging the thus mixed supernatant to form a pellet, resuspending the pellet in aqueous sodium cholate to form a suspension, dialysing the suspension against aqueous sodium cholate to form a solubilised microsome preparation, and purifying the solubilised microsome preparation by column chromatography to obtain a column fraction containing the protein.

The protein is preferably obtainable from human adrenal glands.

The adrenal proteins, especially human adrenal protein, form one aspect of the invention.

Experiments indicate that the protein obtainable by the above techniques is steroid 21-hydroxylase (p450c21). Steroid 21-hydroxylase is an enzyme prominent in the zona glomerulosa of the adrenal cortex and which catalyses one step of the biological pathway from cholesterol to hydrocortisone. cDNA encoding 21-hydroxylase has been cloned and sequenced and an amino acid sequence derived for the protein[10].

The adrenal protein obtainable as described above may be modified by one or more amino acid modifications (deletions, additions or substitutions) which do not cause loss of adrenal autoantibody binding properties.

The protein may be in crude or purified form. Preferably, it is substantially pure. The protein may be native protein derived from a human or animal source or it may be of recombinant origin. The protein may be in the form of a fragment thereof comprising a synthetic peptide.

The present invention further relates to steroid 21-hydroxylase fragments of most surprising identity which are useful in assays for adrenal autoantigen. The invention a/so relates to DNA encoding such fragments and to assays using them.

Thus, the invention provides a polypeptide comprising an amino acid sequence which is shown in the amino acid sequence extending from amino acid residue No. 227 to amino acid residue No. 480 of sequence SEQ ID No 1 and which contains an epitopic region for adrenal autoantibody. In one embodiment such polypeptides also include an amino acid sequence which is shown in the amino acid sequence extending from amino acid residue No. 1 to amino acid residue No. 127 of sequence SEQ ID No. 1.

Also provided by the invention is a polypeptide comprising an epitopic region for adrenal autoantibody and including an amino acid sequence shown in the amino acid sequence extending from amino acid residue No 434 to amino acid residue No 480 of sequence SEQ ID No. 1. Included in the invention is a polypeptide comprising an epitopic region for adrenal autoantibody and an amino acid sequence which is shown in the amino acid sequence extending from amino acid residue No. 227 to amino acid residue No. 480 of sequence SEQ ID No. 1 and which includes amino acid residue No. 434 of sequence SEQ ID No. 1.

The polypeptides of the invention may optionally be modified by one or more amino acid alterations (deletions, additions or substitutions) which do not cause loss of adrenal autoantibody binding properties.

The polypeptides of the invention may be of recombinant origin. The polypeptides may be glycosylated or unglycosylated.

The polypeptides of the invention may be synthetic peptides, synthesised by any known method, for example.

The polypeptides of the invention are useful in assays and may be labelled. In the assay methods, a sample is contacted with a polypeptide of the invention. Preferred features of the assays are described with reference to the assay involving protein obtainable from adrenal glands. Kits comprising a polypeptide of the invention are also provided. Preferred features of such kits are described with reference to kits containing protein obtainable from adrenal glands.

In a further aspect the invention provides DNA sequences encoding a polypeptide of the invention.

The invention in another aspect resides in DNA sequences which encode an epitope to adrenal autoantibody and which comprise a nucleic acid sequence shown in the nucleic acid sequence extending from nucleic acid base No 733 to base No. 1494 of sequence SEQ ID No. 1. Such DNA sequences may also include a nucleic acid sequence shown in the nucleic acid sequence extending from nucleic acid base No 13 to nucleic acid base No 435 of sequence SEQ ID No. 1.

In a yet further aspect the invention provides DNA which encodes an epitope to adrenal autoantibody and which includes a nucleic acid sequence shown in the amino acid sequence extending from nucleic acid base No. 1354 to nucleic acid base No. 1494 of sequence SEQ ID No. 1.

Included in the invention is DNA which encodes an epitope to adrenal autoantibody and which comprises a nucleic acid sequence shown in the nucleic acid sequence extending from nucleic acid base 733 to base No. 1494 of sequence SEQ ID No. 1 and which includes bases Nos. 1354–1356 of sequence SEQ ID No. 1.

In another aspect, the invention comprises DNA sequences encoding an epitope to adrenal autoantibody and consisting of the nucleic acid sequence extending from nucleic acid base No. 733 to base No. 1494 of sequence SEQ ID No. 1 and sequences which have homology to at least part of the aforesaid sequence, encode an epitope to adrenal autoantibody and optionally include bases No. 1354–1356 of sequence SEQ ID No. 1.

The invention also includes DNA sequences which hybridise to any of the above-mentioned sequences and encode a polypeptide comprising an epitope to adrenal autoantigen. The hybridisation conditions used are a matter of individual choice. Hybridisation conditions which may be used to find active sequences include, but are not limited to, 1M NaCl/10×Denhardt's solution/50 mM Tris-HCl (pH 7.4)/10 mM EDTA/0.1% SDS/100 µg/ml denatured herring sperm DNA (Sigma) at 65° C. for 16 h, with the following washing conditions, i.e. 2×SSC/0.1% SDS, 42° C.→0.5×SSC/0.1% SDS, 50° C.→0.1×SSC/0.1% SDS, 65° C.→0.1×SSC/0.1% SDS, 68° C.

The DNA provided by the invention includes DNA sequences degenerate to those described above having regard to the genetic code. Also included are allelic equivalents of the described sequences and their degenerate equivalents.

In other aspects, the invention provides an expression vector comprising DNA of the invention and a host transformed by such an expression vector. The invention also relates to a process for producing a transformant capable of expressing a polypeptide of the invention, comprising transforming a host with an expression vector of the invention.

In yet further aspects, the invention provides a method of preparing a polypeptide of the invention, comprising culturing a transformant capable of expressing such a polypeptide so as to permit expression of the DNA encoding the polypeptide, as well as a process for producing an expression vector of the invention, comprising inserting into a vector capable of transforming a host cell a DNA sequence of the invention in a position permitting expression of the DNA.

The invention includes a method of producing a yeast expression vector comprising a DNA sequence of the invention, comprising (a) replacing the bases coding for the first 13 amino acids of the steroid 21-hydroxylase gene sequence with bases coding for a yeast leader sequence, (b) before or after said replacement digesting the steroid 21-hydroxylase gene sequence with one or more restriction enzymes, such that steps (a) and (b) together result in a DNA fragment with the yeast leader sequence and encoding a polypeptide comprising an epitope to adrenal autoantibody or result in plurality of DNA fragments which may be ligated together to form a DNA sequence encoding such a polypeptide, if necessary providing a stop codon at the 3' end of the fragments or of that one of the plurality of fragments which is to form the 3' end of the coding sequence, and (c) ligating the DNA fragment or fragments into a yeast expression vector.

In one preferred embodiment of step (a), the bases coding for the first 13 amino acids of steroid 21-hydroxylase are replaced with a DNA sequence comprising the first 42 base pairs of coding sequence from the STE2 gene.

Preferably, in step (a), the first 41 base pairs of the steroid 21-hydroxylase gene sequence (21-OH) are removed therefrom and the resultant fragment is ligated into yeast expression vector pYES2, as cut with BamHI and SphI, using a BamHI-NarI linker comprising 11 base pairs of non-coding and 42 base pairs of coding STE2 gene sequence, to prepare a pYES2/21-OH construct. Preferably, in step (b), the construct is digested with BamHI, PvuII and SphI to obtain BamHI-PvuII and PvuII-SphI fragments, which in step (c) are ligated into a yeast expression vector. Preferably the expression vector is constructed by cloning into the EcoRI and SphI sites of pYES2 a linker including one or more stop codons and a restriction site for a restriction enzyme to be used in transforming a host, for example E. Coli.

The invention further provides a yeast expression vector comprising a DNA coding sequence for a polypeptide of the invention ligated at its 5' end to a yeast leader sequence, especially the STE2 leader sequence, and controlled by the GAL1 promoter. Also included are host cells, e.g. E. Coli or Saccharomyces cerevisiae, transformed by such an expression vector or an expression vector obtainable by a method described herein.

In another aspect there is provided a method of producing a yeast expression vector comprising a DNA sequence of the invention, the method comprising ligating into a yeast expression vector a DNA sequence comprising a yeast leader sequence, control sequences and a DNA sequence of the invention in proper reading frame.

In yet other aspects the invention resides in kits for detecting adrenal autoantibodies in a sample. In some embodiments the kit comprises the adrenal protein. In another embodiment it comprises a novel polypeptide of the invention.

The invention opens the way to the therapy of adrenal autoimmune disorders as described more fully hereafter, by the disruption of the lymphocytes involved in the disorder. In particular, the invention provides pharmaceutical formulations comprising a protein or protein fragment as described above, especially a novel polypeptide of the invention.

SEQUENCE LISTING

SEQ ID No. 1 shows the amino acid sequence and nucleic acid coding sequence of steroid 21-hydroxylase and the cleavage sites of restriction enzymes used in experiments described hereinafter. The sequence was obtained from a publically available source and is derived from the work of Whith et al.[10]

SEQ ID No. 2 shows the nucleic acid sequence of a novel linker molecule useful in preparing a polypeptide of the invention and itself the subject of one aspect of the invention.

DESCRIPTION OF THE PREFERRED EMBODIMENTS

Figure 1:
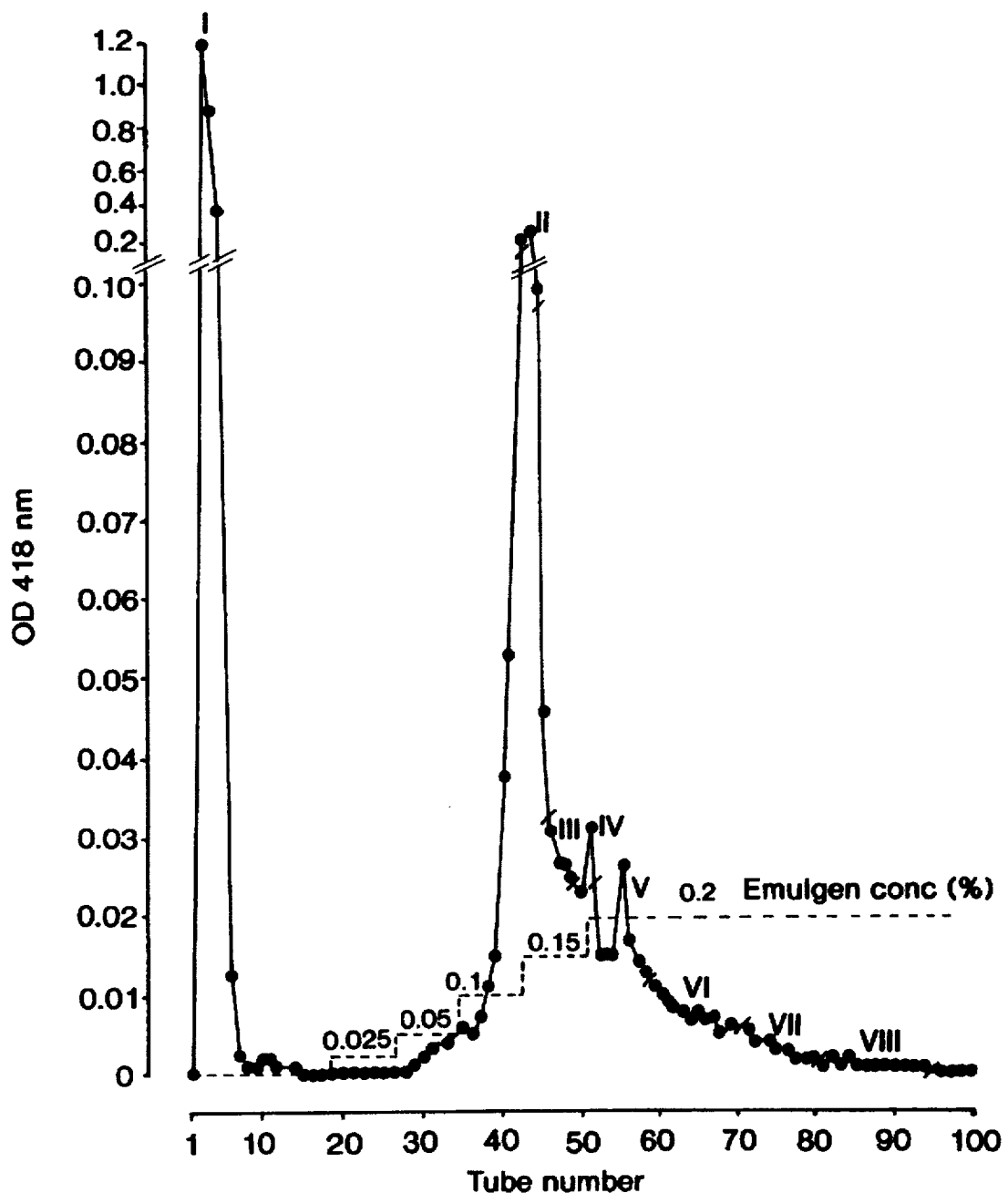
FIG. 1 is an elution profile of proteins eluted from a column chromatograph.

The invention relates to assays for adrenal autoantibodies. The assays involve the use of antigenic protein described in more detail below.

The Antigenic Protein

The protein useful in the invention is a protein obtainable from the microsome fraction of human or animal adrenal glands. The protein is an antigen for adrenal autoantibodies. The protein is further characterised by an observed molecular weight of from about 50,000 to 60,000 and preferably from about 52,000 to 58,000 (eg approximately 55,000). The molecular weight is that observed against the following standards in analysis by gel electrophoresis using a 9% polyacrylamide gel:myosin (205,000), beta-galactosidase (116,000), phosphorylase b (97,000), bovine serum albumin (66,000), ovalbumin (45,000) and carbonic anhydrase (29,000).

The adrenal protein preferably binds to human adrenal autoantibodies but less preferably may bind exclusively to animal adrenal autoantibodies.

The protein may be native protein extracted from human adrenal glands or, less preferably, adrenal glands from another mammal. The protein may be obtained by the following illustrative procedure. Adrenal glands are homogenised and the homogenate subjected to differential centrifugation to obtain a microsome fraction. The microsome fraction is suspended, eg in phosphate buffer containing glycerol.

The suspension is then centrifuged, typically in the presence of sodium cholate and normally also EDTA and dithiothreitol (DTT). After centrifugation polyethylene glycol (PEG) and further sodium cholate and normally glycerol, EDTA and DTT are added to the supernatant and the preparation mixed before further centrifuging. The pellet resulting from centrifuging is resuspended in aqueous sodium cholate normally containing glycerol, EDTA and DTT and dialysed against aqueous sodium cholate, again normally containing glycerol, EDTA and DTT.

After dialysis, the solubilised microsomes are preferably centrifuged, to remove any precipitated material. The solubilised microsome preparation may be stored at −70° C.

Throughout the procedure, the liquids are buffered at pH7, for example using phosphate buffer.

The solubilised microsome preparation is further purified by chromatography, for example using octyl-Sepharose CL-4B and, as the eluant, phosphate buffer (which may contain glycerol, EDTA and DTT), followed by increasing concentrations of one or more detergents, for example that sold under the trade mark EMULGEN.

Column fractions are typically monitored by optical absorbance.

The column fraction containing the adrenal autoantigen may be determined by Western blotting. The column fractions are separated by gel electrophoresis followed by blotting onto nitrocellulose. The nitrocellulose is reacted with serum from a patient with a high level of adrenal autoantibodies and incubated with for example anti-human immunoglobulin-horseradish peroxidase conjugate and, reacted with a chemiluminescent substance. Chemiluminescence is detected with photographic film.

The above procedures are described to illustrate the invention by way of example only, and alternative protocols may be followed to obtain crude, purified or substantially pure antigen.

As described in more detail in the Examples, the adrenal autoantigen isolated by the described procedures was found to have a molecular weight of 55,000±) 5,000. The protein was found to have the biochemical characteristics of steroid 21-hydroxylase and to react on Western blots with rabbit antibodies to recombinant 21-hydroxylase. Absorption of the native human adrenal protein with human adrenal autoantibodies prevented the subsequent reaction of the native human protein with rabbit antibodies to 21-hydroxylase in Western blot analysis. In addition, human adrenal autoantibodies reacted with recombinant 21-hydroxylase expressed in yeast. These experiments indicate that the protein is 21-hydroxylase.

Whilst the adrenal protein is preferably of human origin, the invention embraces antigens derived from animals. The antigen may be obtained by purification of animal or, preferably, human adrenal microsome fractions or by expression of recombinant protein.

As the antigen there may also be used synthetic peptides containing an epitope against adrenal autoantibody. Synthetic peptides may be prepared by any known synthetic procedure, for example. Such synthetic peptides represent a fragment of the native or modified protein.

Steroid 21-hydroxylase

As described elsewhere herein, the adrenal protein has immunological properties which equate it with steroid 21-hydroxylase. Steroid 21-hydroxylase is an enzyme which has been studied because deficiency in 21-hydroxylase activity results in inefficient synthesis of cortisol and elevated levels of corticotropin. Such 21-hydroxylase deficiency is one of several syndromes termed congenital adrenal hyperplasia and is inherited as a monogenic autosomal recessive trait. A plasmid designated pC2/a comprising a portion of the coding sequence of bovine 21-hydroxylase was prepared for use in the diagnosis of congenital adrenal hyperplasia[9]. Plasmid pC21a was subsequently used to prepare a plasmid pC21/3c (pCD//pC21/3c) containing an insert encoding the complete cDNA for 21-hydroxylase except for about 30 base pairs at the 5' end[10].

Plasmid pC21/3c has been sequenced[10] and deposited at the American Type Culture Collection (ATCC) under ATCC Nos 57420 (freeze dried E. Coli containing the plasmid and 57421 (purified plasmid DNA). Both deposits are freely available to the public.

Saccharomyces cerevisiae capable of producing steroid 21-hydroxylase may be made by a method comprising ligating into a yeast expression vector the steroid 21-hydroxylase gene sequence obtainable from plasmid pCD//pC21/3c (ATCC 57421) modified by replacement of the bases coding for the first 13 amino acids with the bases coding for a yeast leader sequence, and transforming saccharomyces cerevisiae with the resultant vector.

Preferably, the steroid 2 1-hydroxylase gene sequence obtainable from said plasmid is subcloned as a BamHI fragment into vector pTZ18, and the resultant vector containing a 21-hydroxylase gene sequence is digested to obtain a fragment comprising a coding region for 21-hydroxylase and ligated into yeast expression vector pYES, as cut with BamHI and SphI, using a BamHI-NarI linker comprising 11 base pairs of non-coding and 42 base pairs of coding STE2 gene sequence.

Included in the invention is a method of producing a yeast expression vector comprising a DNA sequence encoding steroid 21-hydroxylase, comprising ligating into a yeast expression vector the steroid 21-hydroxylase gene sequence obtainable from plasmid pCD//pC21/3c (ATCC 57421) modified by replacement of the bases coding for the first 13 amino acids with the bases coding for a yeast leader sequence and a method of expressing steroid 21-hydroxylase, comprising culturing Saccharomyces cerevisiae transformants prepared by a method of the invention.

Steroid 21-hydroxylase may therefore be used in assays and kits for detecting adrenal autoantibody, especially in the diagnosis of Addison's disease. Steroid 21-hydroxylase may also be used in the therapy of adrenal autoimmune disorders.

The expression of bovine 21-hydroxylase as part of a process for the preparation of steroids is described in EP 0340878 (Gist-Brocades).

The 21-hydroxylase is preferably human 21-hydroxylase, but may alternatively be an animal (e.g. bovine) 21-hydroxylase. The 21-hydroxylase may be purified from human or animal sources but is preferably recombinant 21-hydroxylase. The 21-hydroxylase may have a native sequence or may be modified by one or more amino acid alterations which do not result in loss of antigenicity towards adrenal autoantibodies.

Also useful in the invention are fragments of 21-hydroxylase which retain the desired antigenic property.

The protein or protein fragment may be in crude, purified or pure form.

Cloning Antigenic Protein

Recombinant protein may be prepared by isolating polyadenylated adrenal mRNA and reverse transcribing it into cDNA to prepare a cDNA library. A host organism is transformed with the cDNA using an appropriate expression vector and the transformants screened for organisms expressing the adrenal autoantigen, which organisms may then be cloned. Hosts may be prokaryotic or eukaryotic, for example E. Coli, yeast or CHO cells. Of course, when a host is transformed with a vector, appropriate promoter-operator sequences are also introduced in order for the protein to be expressed. The protein obtained may be glycosylated or unglycosylated.

An illustrative procedure for preparing recombinant adrenal protein will now be described in more detail by way of example only. Polyadenylated adrenal RNA is isolated and the cDNA sequence based on the RNA sequence is generated with the use of reverse transcriptase. The cDNA is then cloned into a bacteriophage vector (eg lambda gt10, lambda gt11, lambda Zap) and an adrenal cDNA library is created. The library is then screened using 32-P labelled oligonucleotide probes synthesised on the basis of known parts of the amino acid sequence of adrenal autoantigen. The library (when subcloned into the expression vector, eg lambda gtl 1) can alternatively be screened with autoantibodies to adrenal antigen or with monoclonal antibodies. In this case the positive plaques are identified in a reaction with radiolabelled Protein A or enzyme-labelled anti-IgG.

Positive plaques (ie containing the cDNA sequence complementary to the probes or expressing the antibody binding protein) are purified to homogeneity and ligated to create a full coding sequence. The full-length cDNA is then sequenced by the Sanger method and subcloned into a plasmid vector, eg pBR322, pTZ18 or Bluescript.

Alternatively, the gene coding for adrenal autoantigen can be synthesised in a polymerase chain reaction (PCR). In this method, the first strand of cDNA is synthesised from RNA using reverse transcriptase and then used as a template for DNA amplification with Taq DNA polymerase. The primers for initiation of each round of amplification are synthesised based on the known amino acid sequence of the N terminus of the adrenal protein. In this case a modification of cDNA amplification using one-sided (anchored) PCR is used. The amplified gene is purified on an agarose gel and cloned into plasmid vectors as above.

For expression of recombinant protein, the full length of the isolated gene is cloned into a mammalian expression vector (eg pRC/CMV). CHO cells, for example, are then transfected (using the $CaPO_4$ precipitation method) with vectors containing the adrenal autoantigen gene. Cells are collected, concentrated by centrifugation and a microsomal preparation prepared. The presence of recombinant proteins in the microsomal fraction is detected by Western blotting using adrenal autoantibodies and the material purified using Octyl Sepharose chromatography as described above in relation to purification of native adrenal autoantigen.

Glycosylation of the recombinant protein may be studied using lectins and compared to the native protein.

Detailed methodology of cloning techniques may be found in J Fambrook; E F Fritch and T Maniatis, Molecular Cloning—A Laboratory Manual, Cold Spring Harbor Laboratory, Cold Spring Harbor, N.Y., Second Edition 1989.

A specific method of expressing human steroid 21-hydroxylase will now be described.

Human 21-hydroxylase may be expressed using the 21-hydroxylase gene in plasmid pCD//pC21/3c[10]. The purified plasmid is publically available from ATCC deposit No. 57421. Alternatively, a suitable plasmid may be prepared following the procedure of White et al[10].

In an exemplary technique, the 21-hydroxylase gene in pCD/pC21/3c was modified by replacing the first 13 amino acids with the first 14 amino acids of STE2 gene and placed under the control of GAL1 promoter in pYES 2.0 (Invitrogen).

In this technique the 21-hydroxylase gene sequence was subcloned from pCD//pC21/3c as a BamHI fragment into the vector pTZ18 (Pharmacia). Digestion with SphI (Northumbria Biologicals Ltd, Cramlington NE23 9HL, UK) followed by partial digestion with NarI (Northumbria Biologicals Ltd, Cramlington NE23 9HL, UK) yielded a large fragment comprising the entire coding region of 21-hydroxylase apart from 41 base pairs at the 5' end. This was then ligated into pYES cut with BamHI (Northumbria Biologicals Ltd, Cramlington NE23 9HL, UK) and SphI using a BamHI-NarI linker comprising 11 base pairs of non-coding and 42 base pairs of STE2 coding sequence[58]. Transformants of Saccharomyces cerevisiae (C13 ABYS 8B—Yeast Genetic Stock Center, Berkeley, Calif.) were grown in selective media and used to inoculate expression cultures in YEP-glucose (2%) or YEP-galactose (2%). [YND is yeast nitrogen base from Difco Laboratories+2% dextrose and YEP is yeast extract+2% peptone (both from Oxoid)]. After 48 hours at 30° C., the cells were harvested, broken by vortexing with glass beads in 1% sodium deoxycholate and analysed on SDS-PAGE followed by Western blotting.

Bovine 21-hydroxylase may be expressed as described in EP 0340878.

The invention therefore provides a method of producing a transformant of Saccharomyces cerevisiae capable of producing steroid 21-hydroxylase, comprising ligating into a yeast expression vector the steroid 21-hydroxylase gene sequence obtainable from plasmid pCD//pC21/3c (ATCC 57421) modified by replacement of the bases coding for the first 13 amino acids with the bases coding for a yeast leader sequence, and transforming Saccharomyces cerevisiae with the resultant vector.

Preferably, the steroid 21-hydroxylase gene sequence obtainable from said plasmid is subcloned as a BamHI fragment into vector pTZ18, and the resultant vector containing a 21-hydroxylase gene sequence is digested to obtain a fragment comprising a coding region for 21-hydroxylase and ligated into yeast expression vector pYES, as cut with BamHI and SphI, using a BamHI-NarI linker comprising 11 base pairs of non-coding and 42 base pairs of coding STE2 gene sequence.

The protein may be a variant of the native form containing amino acid alterations which do not result in loss of antigenicity to adrenal autoantibodies.

Such modified proteins may be prepared, for example, by the use of oligonucleotide directed mutagenesis with a synthetic oligonucleotide (typically 7 to 24 bases long) that is complementary to the wild-type sequence but which contains one or more base changes compared to the wild-type sequence.

The size of the oligonucleotide primer is determined by the requirement for stable hybridization of the primer to the region of the gene in which the mutation is to be induced, and by the limitations of the available methods for synthesizing oligonucleotides. In general the overall length of the oligonucleotide will be such as to optimize stable, unique hybridization at the mutation site with the 5' and 3' extensions from the mutation site being of sufficient size to avoid editing of the mutation by the exonuclease activity of the DNA polymerase. Oligonucleotides used for mutagenesis usually contain from about 7 and more usually about 12 to about 24 bases, preferably from about 14 to about 20 bases and still more preferably from about 15 to about 18 bases. They will usually contain at least about three bases at the centre or positions immediately 3' of the centre of the altered or missing codon.

The primer is hybridized to single-stranded phage such as M13 into which a strand of DNA of the invention has been cloned. It will be appreciated that the phage may carry either the sense strand or antisense strand of the DNA. When the phage carries the antisense strand the primer is identical to the region of the sense strand that contains the codon(s) to be mutated except for a mismatch with said codon(s) that defines a deletion of the codon or a triplet that codes for another amino acid.

When the phage carries the sense strand the primer is complementary to the region of the sense strand that contains the codon(s) to be mutated except for an appropriate mismatch in the triplet that is paired with the or each codon to be mutated. The hybridization is carried out at a temperature which will usually range between about 0° C. and 70° C., more usually about 10° C. to 50° C.

Melting temperature (Tm) of synthesised oligonucleotides is calculated and used as a guidance to hybridisation temperature conditions. Usually the template and the oligonucleotides are heated briefly to 20° C. above the estimated Tm. Hybrids form as the temperature of the reaction mixture drops below Tm. The resulting mixture of double-stranded heteroduplex DNA is then transfected directly into a bacterial host and mutants can be identified by screening plaques by hybridisation, using the radiolabelled mutagenic oligonucleotide as a probe. Hybridisation is usually carried out under conditions that allow the labelled oligonucleotide to form hybrids with both mutant and wild-type DNA. By progressively increasing the stringency of the subsequent washes it is possible to establish conditions under which hybrids between mutagenic oligonucleotide and wild-type DNA will dissociate and perfect hybrids formed by the oligonucleotide and desired mutant will not dissociate. Identified in this way mutants are then purified and the presence of the desired mutation confirmed by DNA sequencing of the mutagenised and adjacent regions or of the full insert sequence carried in the vector.

After the hybridization, the primer is extended on the phage DNA by reaction with DNA polymerase I, $T_4$ DNA polymerase, reverse transcriptase or other suitable DNA polymerase. The resulting dsDNA is converted to closed circular dsDNA by treatment with a DNA ligase such as $T_4$ DNA ligase. DNA molecules containing single-stranded regions may be destroyed by S1 endonuclease treatment.

The resulting mutational heteroduplex is then used to transform a competent host organism or cell. Replication of the heteroduplex by the host provides progeny from both strands. Following replication the mutant gene may be isolated from progeny of the mutant strand, inserted into an appropriate expression vector, and the vector used to transform a suitable host organism or cell. Exemplary vectors and hosts are described above.

Directed mutagenesis techniques are well known and are described in the literature[24-28].

The invention accordingly includes not only DNA sequences encoding protein of the invention but also DNA sequences which hybridise to such sequences and encode an antigenic determinant to adrenal autoantibody. Such hybridisable sequences may be sequences encoding a modified protein or a protein fragment, whether of modified or unmodified protein. Hybridisation conditions are described, for example, by Smith M and Gillam S[25] and by Fambrook et al. (supra). Modified DNA is normally capable of hybridising to DNA sequences encoding protein of the invention under conventional hybridising conditions and preferably under stringent hybridising conditions.

Polypeptides

The invention relates also to the preparation of polypeptides antigenic to adrenal autoantibody and the use of such polypeptides in assays. In accordance with the invention, such polypeptides comprise an amino acid sequence of a region of steroid 21-hydroxylase towards its carboxyl terminal end. The polypeptides may be modified by one or more amino acid alterations (additions, deletions or substitutions) so long as they retain the property of binding to adrenal autoantibody.

The fragment between amino acid residues 227 and 480 of the accompanying sequence listing SEQ ID No. 1 binds effectively to adrenal autoantibody. It is most surprising that the binding sites is in a region at the carboxyl terminal end.

The polypeptides comprise an epitope to adrenal autoantibody and preferably comprise an amino acid sequence which is shown in the amino acid sequence extending from amino acid residue 227 to amino acid residue 480 of SEQ ID No. 1. Amino acid and nucleic acid sequences defined herein by reference to the terminals residues of the sequence are inclusive of the terminal residues. Residue 480 is the final amino acid at the carboxyl terminal of steroid 21-hydroxylase. In preferred embodiments, the polypeptides comprise an amino acid sequence which is shown in the amino acid sequence extending from amino acid residue 494 to amino acid residue 230, 240, 250, 260, 270, 280, 290, 300, 310, 320, 330, 340, 350, 360, 370, 380, 390 or 400.

The region between amino acid residues 434 and 480 has been shown to be important for autoantibody binding. The invention therefore includes polypeptides which include a sequence comprising residue 434 (e.g. the sequence extending from residue 434 to residue 480) and an epitope for adrenal autoantibody. Also included are those polypeptides which include a sequence comprised in the region between residues 433 and 480, for example polypeptides including at least the sequence between residues 400 and 480.

The polypeptides may be recombinant or synthetic for example.

DNA

DNA sequences coding for the polypeptides of the invention are therefore included in the invention. Also included is DNA comprising a coding sequence shown in SEQ ID No. 1 and encoding an epitope to adrenal autoantibody. Further included are DNA sequences coding for polypeptides which bind to adrenal autoantibody and which hybridise to DNA comprising a sequence shown in SEQ ID No. 1 and encoding a polypeptide of the invention. Thus, the invention provides DNA sequences which encode an epitope to adrenal autoantibody and which comprise a nucleic acid sequence shown in the nucleic acid sequence extending from nucleic acid base No 733 to base No. 1494 of sequence SEQ ID No. 1. Such DNA sequences may also include, for example, a nucleic acid sequence shown in the nucleic acid sequence extending from nucleic acid base No 13 to nucleic acid base No 435 of sequence SEQ ID No. 1.

The region between bases 1354 and 1494 has been shown to encode an amino acid sequence important for autoantibody binding. The invention therefore includes DNA sequences which include a sequence comprising base 1354 (e.g. the sequence extending from base 1354 to base 1356 or from 1354 to base 1394 and encoding an epitope to adrenal autoantibody.

The invention includes DNA sequences which hybridise to those described above and encode an epitope to adrenal autoantibody. Sequences degenerate to those previously described, allelic equivalents and their degenerate equivalents are included.

The DNA is expressed by being incorporated into an expression vector which in turn is used to transform a host, e.g. E. Coli or S. Cerevisiae, which expresses the polypeptide.

DNA encoding a polypeptide of the invention may be prepared using the pYES2/21-OH construct previously described.

Preparation of a DNA Sequence and Polypeptide

In an exemplary experiment, the pYES2/human 21-OH construct under control of the GAL1 promotor including the yeast STE2 leader sequence was modified by cloning a unique linker designed to include useful restriction sites and introduce translation stop codons (TGA). A series of truncations and deletions 3' from the leader sequence have been made, expressed in yeast and tested for binding to rabbit antibody to 21-OH and adrenal autoantibody. The truncations and deletion were made using PvuII, SauI, PmaCI and StuI.

In addition, protein expression and reaction with antibodies have been analysed using an in vitro translation system.

A deletion between the two PvuII sites had no effect on antibody and autoantibody binding to recombinant protein. The truncations at the SauI and PmaCI sites resulted in loss of the ability of recombinant protein to bind rabbit antibody and autoantibody. Recombinant 21-OH after truncation at the StuI site reacted with rabbit antibody but not with adrenal autoantibody. Addison pool serum and four individual sera from patients with high levels of adrenal autoantibody were used in these experiments. The full-length construct and all modified constructs were expressed in Saccharomyces Cerevisiae and using an in vitro coupled reticulocyte lysate translation system (sold under the trade mark TNT by Promega Corp., 2800 Woods Hollow Road, Madison, Wis 53711-5399, USA). Expressed proteins were analysed by western blotting using rabbit antibody and Addison sera. In addition, the recombinant protein in this system labelled with 35-S-methionine and analysed on SDS-PAGE followed by autoradiography.

Antibodies to the Antigenic Protein

In some assays, antibodies to the adrenal protein are useful. Such antibodies may be prepared by any known method, for example.

Polyclonal antibodies may be prepared by administering the adrenal autoantigen or cells expressing the antigen to an animal in order to induce the production of serum containing polyclonal antibodies.

Monoclonal antibodies can be prepared using the hybridoma technique of Kohler and Milstein[29]. Further exemplary literature references are listed in the attached bibliography[30-34]. According to the hybridoma method, a human or other animal or lymphocytes therefrom is/are immunised with a protein or protein fragment of the invention. Lymphocytes from the immunised individual or culture are fused with myelomas into single cells. The resulting continuous cell lines are screened for antibody producing hybrids. Such hybrids may be cultured and the antibody collected.

The antibodies useful in the invention include not only intact molecules, including human monoclonal antibodies, but also fragments thereof which are capable of binding to the antigenic protein. Also useful are recombinant antibodies.

Antibodies to 21-hydroxylase may be made by such techniques as described above.

Labelling

The assays of the invention normally involve antigen or antibody labelled so as to be detectable. Numerous methods of labelling are known and any such known technique may be used, for example. Examples of the extensive literature describing labelling techniques are to be found in the attached bibliography[35].

Exemplary labels are radioactive labels, enzymes, fluorescent compounds, chemiluminescent compounds, bioluminescent compounds and metal chelates. The binding of such labels to the antigen or antibody may be performed using any conventional technique, for example.

Assays

The assays of the invention include those assays known to the skilled person for the quantitative or non-quantitative detection of antibodies and all involve contacting antigenic polypeptide (the adrenal protein obtainable as previously described or fragments thereof, for example the polypeptides of the invention) with a sample. A suitable polypeptide for performing an assay is that obtained using the steroid 21-hydroxylase gene with the PvuII-PvuII deletion. The assays may be competitive or non-competitive and examples are radioimmunoassays (RIA), enzyme immunoassays (EIA), and enzyme-linked immunosorbent assays (ELISA). The reader is referred to the literature for details of suitable assays[35].

The competitive assays of the invention include assays which involve contacting an antigenic polypeptide (which expression embraces protein and protein fragments) with a biological sample (typically serum or urine). Normally the sample is diluted, for example, 1 part sample in from 10 to 30 parts diluent such as phosphate buffered saline or another buffer. Either simultaneously or subsequently there is added labelled antibody against the antigenic polypeptide. The labelled antibody and any antibody in the sample compete to bind to the antigen and the bound labelled antibody after competition is measured. The antigenic polypeptide in such techniques is preferably immobilised on a substrate by known techniques such as covalent bonding via an amide or ester linkage or adsorption, for example.

The invention also includes sandwich assays (eg RIA, EIA, ELISA) in which the antigenic polypeptide immobilised on a substrate is contacted with a biological sample suspected of containing adrenal autoantibodies. After washing, there is added labelled antigenic polypeptide or labelled anti-adrenal autoantibody antibody, either of which selectively binds to any adrenal autoantibody which has bound to the immobilised antigen. The appropriate detection technique for the label is then employed, eg quantitative or non-quantitative detection of radioactive emissions or colorimetric techniques. Sandwich assays can also be employed using, as the labelled ligand for the antibody, any agent capable of recognising an antibody, for example labelled anti-immunoglobulins, protein A or protein G.

Other assays comprise contacting a sample with labelled antigenic polypeptide (e.g. protein), separating bound and unbound labelled antigen (eg using a column having adsorbed thereon antibody to the antigen) and detecting the labelling by a quantitative or non-quantitative technique.

Assays may also be performed by contacting with a sample immobilised anti-antigenic protein antibody having bound thereto labelled antigen and detecting labelled antigen bound to immobilised antibody or labelled antigen bound to antibody in the sample.

Two Illustrative Assay Techniques for Adrenal Autoantibodies

1. Assay based on a radioactive label

Purified adrenal autoantigen is labelled with a radioactive label such as $^{125}I$ using one of many well-known techniques. The labelled material will then be incubated (1h at room temperature) with a suitably diluted (eg 1 in 20 in phosphate buffered saline) serum sample. Adrenal autoantibodies present in the test sample will bind to the $^{125}I$-labelled adrenal autoantigen and the resulting complex is precipitated by addition of antibodies to human immunoglobulins or addition of a similar reagent (eg solid phase Protein A). The amount of $^{125}I$-labelled antigen in the precipitate is then determined. The amount of adrenal autoantibody in the test serum sample will be a function of the amount of radioactivity precipitated. The amount of adrenal autoantibody can be expressed as the amount of radioactivity in the pellet or more usually by including dilution of an adrenal autoantibody positive reference serum in the assay.

2. Assay based on an enzyme label

Purified adrenal autoantigen is coated onto plastic wells of ELISA plates either directly onto plain wells or indirectly. The indirect method could involve coating the wells first with a monoclonal or polyclonal antibody to adrenal autoantigen (the antibody would be selected so as not to bind to the same site as adrenal autoantibodies) followed by addition of adrenal autoantigen. Several other indirect coating methods are well known.

After coating with autoantigen, suitably diluted (eg 1 in 20 in phosphate buffered saline) test sera are added to the wells and incubated (1 h at room temperature) to allow binding of adrenal autoantibody to the antigen coated onto the wells.

The wells are then washed and a reagent such as anti-human IgG conjugated to horseradish peroxidase is added. After further incubation (eg 1 h at room temperature) and washing, an enzyme substrate such as orthophenylene diamine is added and the colour generated measured by light absorbance. The amount of adrenal autoantibody in the test sample will be a function of the final colour intensity generated. Results can be expressed as light absorbance or more usually by including dilution of an adrenal autoantibody positive reference serum in the assay.

The assays of the invention involving the interaction of antigenic polypeptide (e.g. protein) and a sample may be performed using a kit comprising antigenic protein. The sandwich assays of the invention may conveniently be performed using a kit comprising an antigenic polypeptide, normally immobilised on a substrate, and labelled anti-adrenal autoantibody antibody or labelled antigenic polypeptide.

The invention also includes kits for use in competitive assays comprising antigenic polypeptide (the adrenal protein obtainable as previously described or fragments thereof, for example the polypeptides of the invention) and labelled antibody to the antigenic polypeptide. The antigenic polypeptide is preferably immobilised on a substrate. Such kits may further comprise a labelled ligand for adrenal autoantibody as described above.

Further included in the invention are kits comprising labelled antigenic polypeptide for use in simple assays involving detection of antigen/antibody complex. Other kits of the invention comprise anti-antigenic polypeptide antibody which is immobilised on a substrate and which has bound thereto labelled antigenic protein.

In those kits comprising immobilised polypeptide, the protein is preferably immobilised on the internal surface of a plastics tube.

The invention includes assays and kits as described above but which use 21-hydroxylase as the antigen.

In a variant of the invention, the antigenic polypeptide is replaced by antibody to the autoantibody. This variant is not suitable for sandwich assays using ligands which bind to any antibody.

The invention also includes the use of antibody against the adrenal protein or polypeptides of the invention to detect 21-hydroxylase. Methods and kits as described above may be used for such assays. The antibody may be human monoclonal antibody but alternatively is human polyclonal antibody or animal polyclonal or monoclonal antibody. Optionally, the antibody used in assays of the invention may comprise more than one antibody.

Therapy of Adrenal Autoimmune Disease

It is thought that autoimmune diseases are caused at least in part by autoantigens persistently activating T cells[36]. The autoantigen in the case of adrenal autoimmune disease can be any epitope of the antigenic molecule which is recognised by a T cell receptor capable of helping a B cell make antibody to the antigenic molecule, or a T cell otherwise involved in the autoimmune disorder.

Adrenal autoimmune disorders should therefore be treatable by disrupting the action of T cells involved in the disorder. T cells such as, for example, those infiltrating the adrenal gland, in lymphoid organs or in the circulation can act as T helper (Th) cells in responding to adrenal autoantigen epitopes. Such Th cells help B cells make specific anti-autoantigen antibodies. T cells can also act in mediating cell-mediated immune responses and act on adrenal cortex cells by the release of cytokines or directly. The destruction of adrenal cortex cells can result, when cytotoxic T cells specific for the adrenal autoantigen are activated, or by an inflammatory response mediated by a different T cell class.

If such T cells were interfered with, the production of anti-autoantigen antibodies and of T cells destructive of adrenal cortex cells would be suppressed. The T cells could be disrupted by a polypeptide (for example a protein, a protein fragment or a synthetic peptide) capable of binding to the T cell receptor (TCR) of an adrenal autoantigen specific T cell, ie containing a T cell eptiope of the autoantigen.

Such a polypeptide acts as a competitive antagonist for the autoantigen in the adrenal cortex and thereby inhibits antigen specific cellular interactions which result in the production of adrenal autoantibody or adrenal autoantigen specific cell-mediated immunity. Exemplary references describing the use of peptides to treat autoimmune disease are included in the attached bibliography[36-42].

Another therapeutic approach is to suppress the autoimmune response to adrenal autoantigen by administering adrenal autoantigen specific T cells[43-49] or a polypeptide (e.g. a protein or protein fragment) mimicking the TCR of such cells[48, 49]. Administration of such a "vaccine" induces "counter-autoimmunity" which is thought to be mediated by T cells specific to the TCR of the autoimmune T cells[43,48, 50,51].

The autoimmune response may also be suppressed by T suppressor (Ts) cells capable of specifically recognising an anti-adrenal autoantigen B cell or T cell[52,53]. Such therapy may be effected by administering to the patient a polypeptide—e.g. a protein or protein fragment—comprising an adrenal autoantigen epitope capable of inducing Ts cells or by administering adrenal autoantigen—specific Ts cells capable of suppressing an anti-adrenal autoantigen response.

The T cell epitope or epitopes of adrenal autoantigen may be determined by, for example, standard techniques in the art.

The autoimmune TCR specific to the adrenal autoantigen may be characterised using methods described in the literature[54]. Disruption of interaction of the autoimmune T cells with the adrenal autoantigen may alleviate or prevent adrenal autoimmune disease. T cells which will disrupt such interaction and which are specific for the autoimmune TCR for adrenal autoantigen may be prepared[55].

The present invention provides pharmaceutical (including veterinary pharmaceutical) formulations comprising the adrenal protein obtainable from human or animal adrenal glands as defined above, which protein may optionally be modified by one or more amino acid alterations. The invention also includes formulations comprising a fragment of such protein, eg a peptide containing an antigenic determinant to adrenal autoantibody, especially the novel polypeptides described herein.

In another aspect, the invention provides pharmaceutical formulations comprising steroid 21-hydroxylase or a fragment thereof, eg a peptide containing an antigenic determinant to adrenal autoantibody, especially a novel polypeptide of the invention.

The invention also includes pharmaceutical formulations comprising a ligand, eg a peptide, capable of binding to the TCR of an adrenal autoantigen specific T cell or B cell.

In other aspects, the invention provides T cells specific for adrenal autoantigen and polypeptides (e.g. proteins or protein fragments) which mimick the receptor of such T cells. Included in the invention are counter-autoimmune T cells, ie T cells induced by such adrenal autoantibody specific T cell or TCR mimicking pelypeptide (e.g. protein or protein fragment). Pharmaceutical preparations including any of the aforesaid agents are further provided by the invention.

Also provided by the invention are Ts cells capable of interacting specifically with an anti-adrenal autoantigen B cell or T cell and pharmaceutical formulations comprising such cells. Similarly included is the use of the adrenal protein defined above or of an 21-hydroxylase or a fragment of either (eg a peptide comprising a suitable epitope) to generate such anti-autoimmune T cells.

Other Uses of the Antigenic Proteins/Polypeptide

Antigenic protein/polypeptide may be used to purify adrenal autoantibody, for example by adsorbing the antigen or on a substrate, passing a sample containing the antibody over the substrate and then washing the substrate to release the antibody.

The adrenal autoantibody may be used to raise antibody to the adrenal autoantibody for use in assays or, for example, for screening transformed host cells to detect expression of recombinant adrenal autoantibody, which itself could be labelled and used in a competitive assay, for example.

EXAMPLE 1

Preparation and Solubilisation of Adrenal Microsomes

Human adrenal glands were recovered from the redundant tissue surrounding kidneys removed from cadaveric donors and then stored at −70° C. in small (100 mg) pieces. A microsome fraction was isolated from adrenal tissue homogenates by differential centrifugation[11–13] and suspended in 100 mM phosphate buffer pH 7.0 containing 20% glycerol (1 ml of buffer for each g of starting adrenal tissue). The protein concentration was then estimated[14] and the mixture adjusted to a final concentration of 25–30 mg of adrenal protein per ml.

Sodium cholate (solid) was then added to a final concentration of 3 mg of cholate per 1 mg of adrenal proteins and the mixture was adjusted to a final concentration of 0.1 mM EDTA and 0.1 mM dithiothreitol (DTT). Sodium cholate was allowed to dissolve by mixing on a magnetic stirrer at 4° C. for 1 h and then the mixture was centrifuged at 100,000×g for 1 h at 4° C. After centrifugation, an equal volume of 50% PEG 6000 in 100 mM phosphate buffer pH 7.0, 20% glycerol, 0.1 mM DTT, 0.1 mM EDTA was added to the supernatant and the preparation mixed on a magnetic stirrer for 30 min at 4° C. This was followed by centrifugation at 12,000×g for 1 h at 4° C. The pellet was then resuspended in 3% sodium cholate in 100 mM phosphate buffer pH 7.0 containing 20% glycerol, 0.1 mM EDTA, 0.1 mM DTT (1.3 ml per 1g equivalent of starting adrenal tissue) and dialysed overnight at 4° C. against 0.3% sodium cholate in 50 mM phosphate buffer pH7.0, 20% glycerol, 0.1 mM EDTA, 0.1 mM DTT (basal buffer). After dialysis the solubilised microsomes were spun at 12,000×g for 15 min at 4° C. to remove any precipitated material.

The protein concentration of the solubilised microsome preparation was then estimated[10] and the preparation stored in aliquots at −70° C.

EXAMPLE 2

Purification of Adrenal Autoantigen

The methods described by Kominami et al[15] and Bumpus and Dus[16] were used. In particular, Octyl-Sepharose CL-4B (Pharmacia LKB) was extensively washed in 50 mM phosphate buffer pH 7.0, 20% glycerol, 0.1 mM EDTA, 0.1 mM DTT according to the manufacturer's instructions, poured into 1×10 cm column and equilibrated with basal buffer.

6 ml aliquots of solublished microsomes were applied to the column at 25 ml/h and eluted initially with basal buffer. 3.3 ml fractions were collected and monitored by light absorbance at 280 nm and 41 8 nm. Washing of the column was continued until the OD 280 nm was below 0.01 and OD 418 nm was zero. Further elution from the column was then carried out using increasing concentrations of Emulgen 913 (Kayo-Atlas, Tokyo) in the basal buffer (step-wise increases; 0.025%, 0.05%, 0.1%, 0.15% and 0.2%; 25 ml each step).

The column fractions were monitored at 418 nm (monitoring at 280 nm is not possible in the presence of Emulgen) and aliquots (0.5 ml) taken from each fraction. The elution profile of proteins from the column is shown in FIG. 1. Aliquots from groups of fractions were then pooled, concentrated (Centricon 10 microconcentrators) and analysed by gel electrophoresis. In particular, samples from the Octyl-Sepharose column were analysed on polyacrylamide gels (9%) under reducing conditions[17]. A mixture of molecular weight markers containing myosin (205,000), beta-galactosidase (116,000), phosphorylase b (97,000), bovine serum albumin (66,000), ovalbumin (45,000) and carbonic anhydrase (29,000) was run on each gel. After electrophoresis, gels were either stained with coomassie blue, fixed and dried or blotted onto nitrocellulose membranes.

In some experiments, protein bands of interest were cut out from the stained gel and the protein electroeluted (40V and 70 mA for 20 hours) into 0.1M sodium bicarbonate pH 7.8 containing 0.1% SDS. The eluted material was then dialysed extensively against distilled water, dried under vacuum and stored at −40° C.

After proteins were blotted onto nitrocellulose membranes, the membranes were cut into strips and incubated in phosphate buffered saline (PBS) at 37° C. overnight with gentle shaking. The membranes were then reacted with 10% newborn calf serum (NCS) in PBS containing 0.5% Tween 20 for 2 h at 37° C. with gentle shaking. After rinsing and washing with PBS containing 0.5% Tween 20 (3×) 5 ml) followed by reaction with serum from a patient with high levels of adrenal autoantibodies or with normal serum diluted 1:400 in 10% NCS, 10% glycerol, 1M glucose in PBS with 0.5% Tween 20 for 2 h at 37° C. with gentle shaking, the membranes were washed extensively with PBS containing 0.5% Tween 20. They were then incubated with dilute anti-human immunoglobulin-horseradish peroxidase conjugate in PBS containing 0.05% Tween 20 for 1 h at room temperature with gentle shaking. This was followed by washing with PBS containing 0.5% Tween 20 and reaction with a chemiluminescence generating substrate according to the substrate manufacturer's protocol (ECL System from Amersham). Nitrocellulose membrane strips and photographic film were set for 10–60 seconds and then developed.

Experiments were also performed in which rabbit antibody to recombinant steroid 21-hydroxylase[56] and rabbit antibody to microsomal epoxide hydrolase[57] were used in combination with anti-rabbit IgG horseradish peroxidase conjugate.

EXAMPLE 3

Analysis of Electrophoresis Gel

Figure 2:
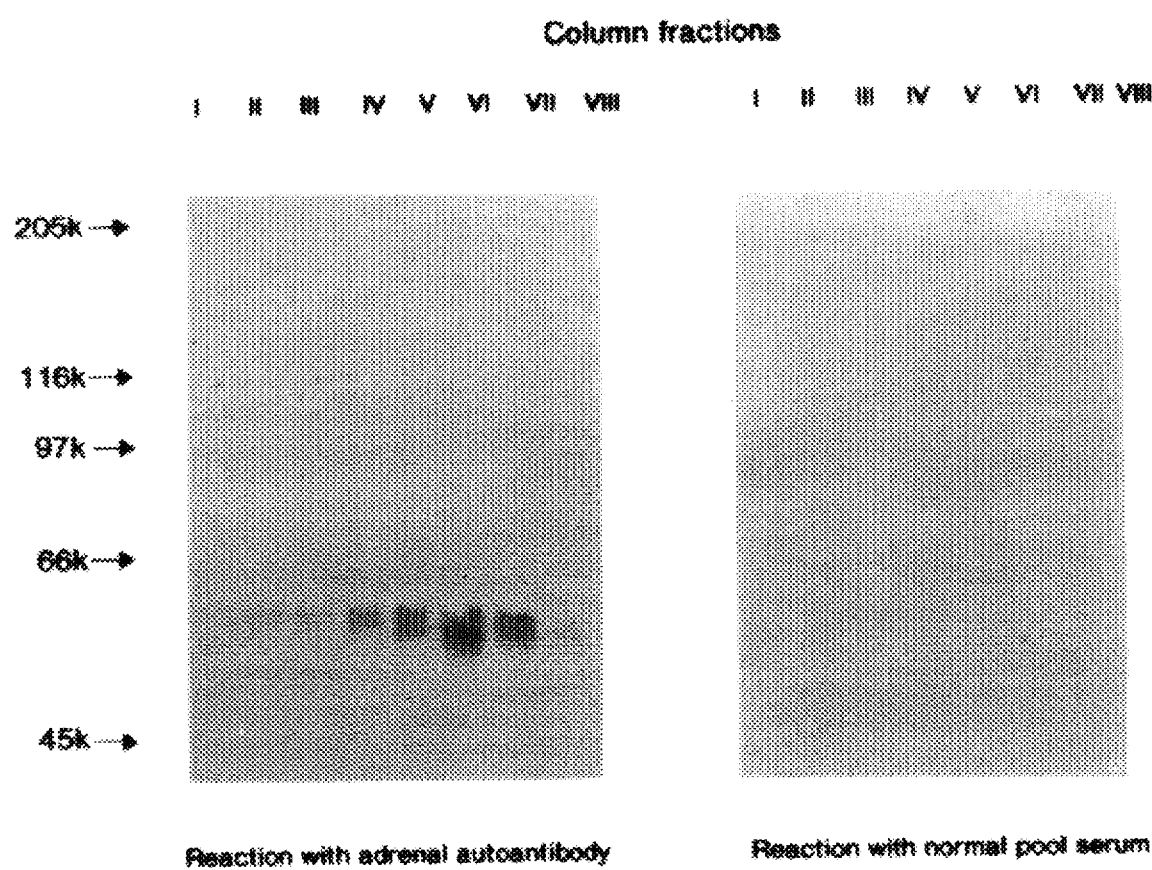
FIGS. 2A and 2B show Western blots of eluted column fractions contacted with (FIG. 2A) serum containing adrenal autoantibodies and (FIG. 2B) normal serum.

As can be seen in FIG. 2A the adrenal autoantibodies only reacted with protein bands with an observed molecular weight of 55,000±5,000. In further studies, the 55,000 mol. wt. band of fraction VI was cut out of the gel, electroeluted and re-run in the gel electrophoresis system. This showed that the protein migrated as a single band with mol. wt. 55,000. In addition, when the electroeluted material was blotted into nitrocellulose, it reacted strongly with adrenal autoantibodies. These studies indicated that 55,000 molecular weight protein is the major adrenal autoantigen involved in autoimmune Addison's disease.

Figure 3:
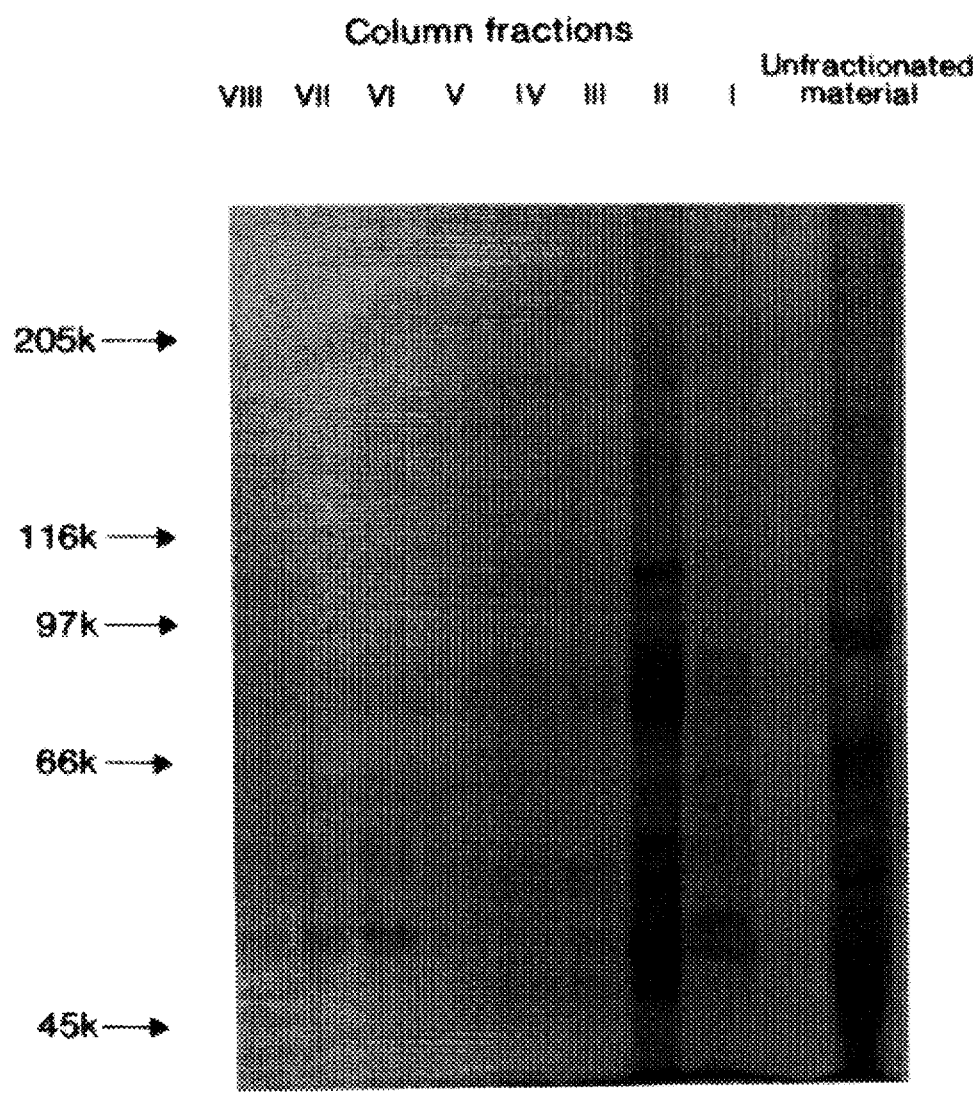
FIG. 3 shows the protein staining pattern of eluted column fractions after gel electrophoresis.

Protein staining of the gel obtained by electrophoresis of the column fractions showed that fraction VI contained a protein with a molecular weight of 55,000 (FIG. 3). Some of the fractions surrounding fraction VI also contained smaller amounts of the 55,000 mol. wt protein.

Figure 6:
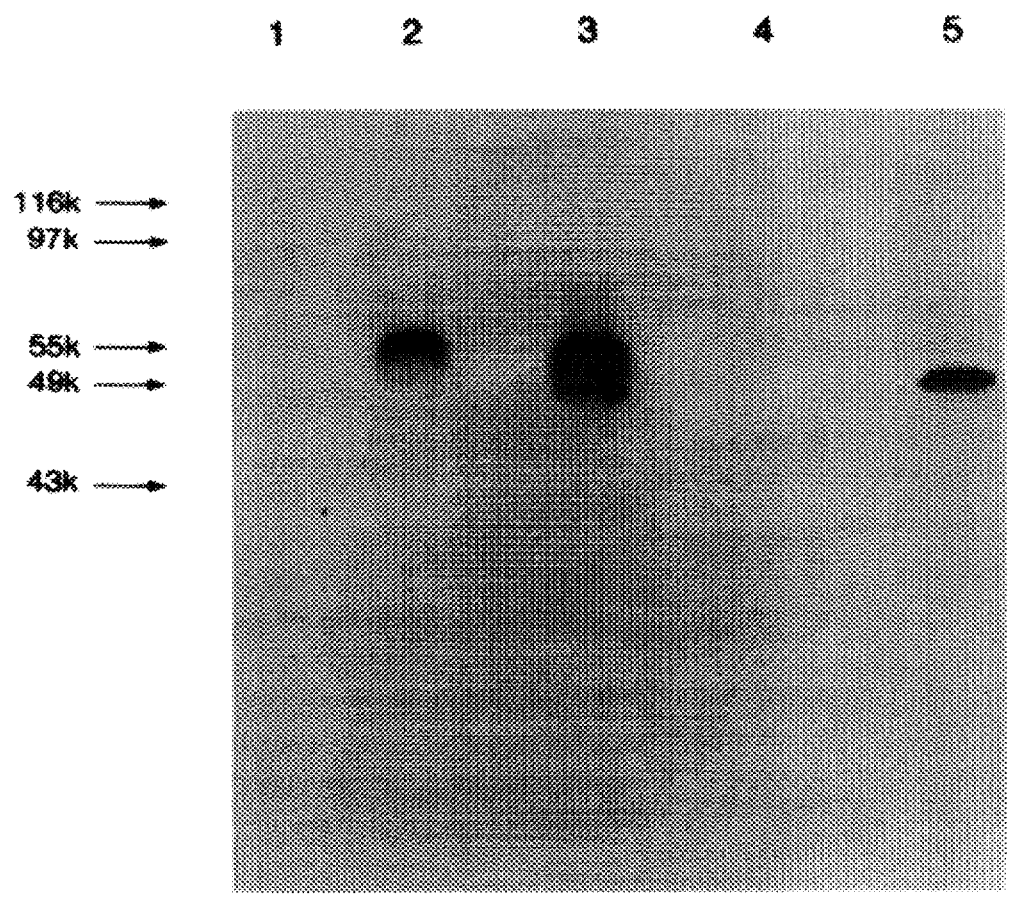
FIG. 6 is a Western blot analysis of eluted column fraction VI.
Figure 7:
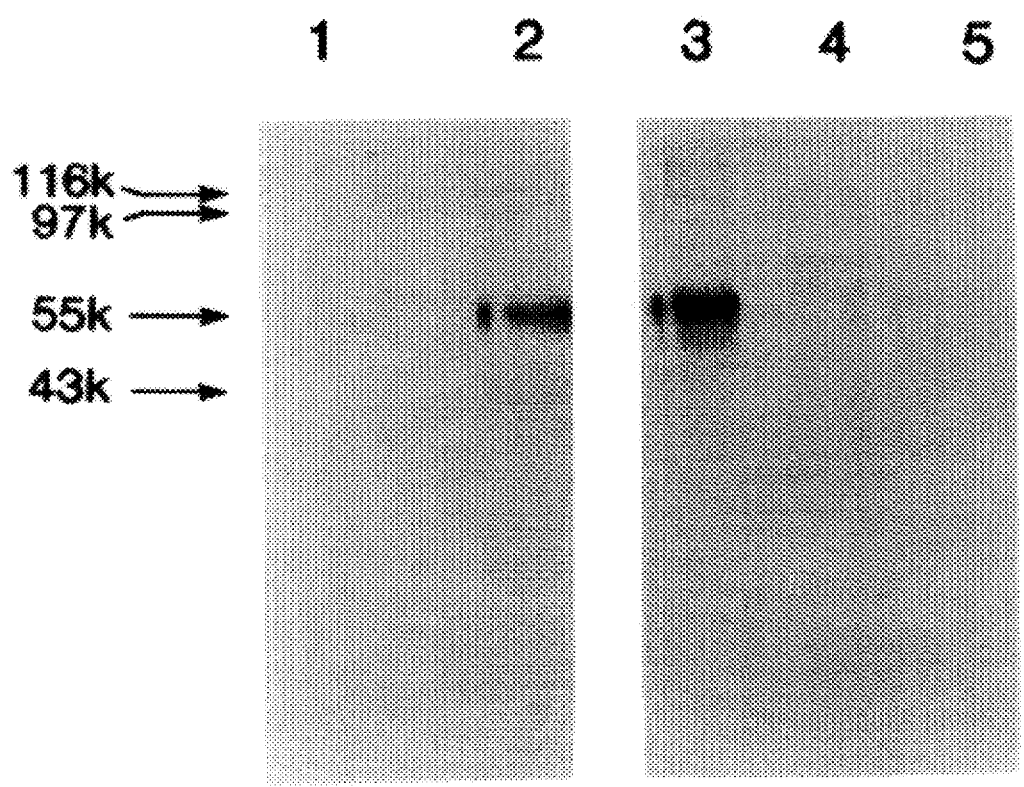
FIG. 7 is a Western blot analysis of the protein of column fraction VI after SDS-PAGE analysis and electroelution.

A further Western blot analysis of fraction VI is shown in FIG. 6, in which Lane 1 shows reaction with normal pool serum, lane 2 reaction with adrenal autoantibody positive pool serum, lane 3 reaction with rabbit 21-hydroxylase antibody, lane 4 reaction with normal rabbit serum and lane 5 reaction with rabbit epoxide hydrolase antibody. The rabbit antibody to 21-hydroxylase, is shown to react with the 55,000 mol. wt. protein whereas the antibody to epoxide hydrolase reacted with a protein of molecular weight 49,000.

In some experiments, the 55k band from SDS-PAGE analysis of fraction VI was cut out of the gel, electroeluted, run on PAGE to confirm homogeneity (data not shown) and analysed by Western blot. The eluted band reacted strongly with adrenal autoantibody positive serum and with rabbit antibody to 21-hydroxylase but not with epoxide hydrolase antibody nor with normal pool human serum, nor with normal rabbit serum.

These observations indicate that the autoantigen is steroid 21-hydroxylase and that a previous suggestion that it is epoxide hydrolase (UK patent application No. 9205040.0) resulted from sequencing the wrong band on a gel.

EXAMPLE 4

Absorption of Adrenal Antigen with Adrenal Antibodies

IgG was purified from normal pool sera and individual patient sera using chromatography on protein A-glass bead columns (Bioprocessing Consett, UK).

Aliquots of purified adrenal protein were incubated with the IgGs (2-5 mgml$^{-1}$) for 1 h at 37° C. A protein A-glass bead suspension in PBS was then added to bind free IgG and IgG complexed to adrenal antigen(s). After 1 h at room temperature, the mixture was centrifuged (12,000xg, 10 min, 4° C.) and the supernatants analysed by SDS-PAGE and Western blotting using Addison sera and rabbit antibodies to recombinant 21-hydroxylase.

Analysis of the Western blots indicated that rabbit antibody to recombinant 21-hydroxylase did not react with native adrenal 55k protein which had been pre-absorbed with IgG from human adrenal autoantibody positive Addison sera (data not shown). Pre-absorption with normal pool serum IgG had no effect on reactivity with 21-hydroxylase antibody.

EXAMPLE 5

Assay for Adrenal Autoantibodies Using Adrenal Autoantigen

Multiple small (1ul) aliquots of fractions I–VIII from the experiment shown in FIG. 1 were blotted into nitrocellulose membranes. The membranes were cut into strips and washed and reacted with serum containing adrenal autoantibodies or normal pool serum.

Figure 4:
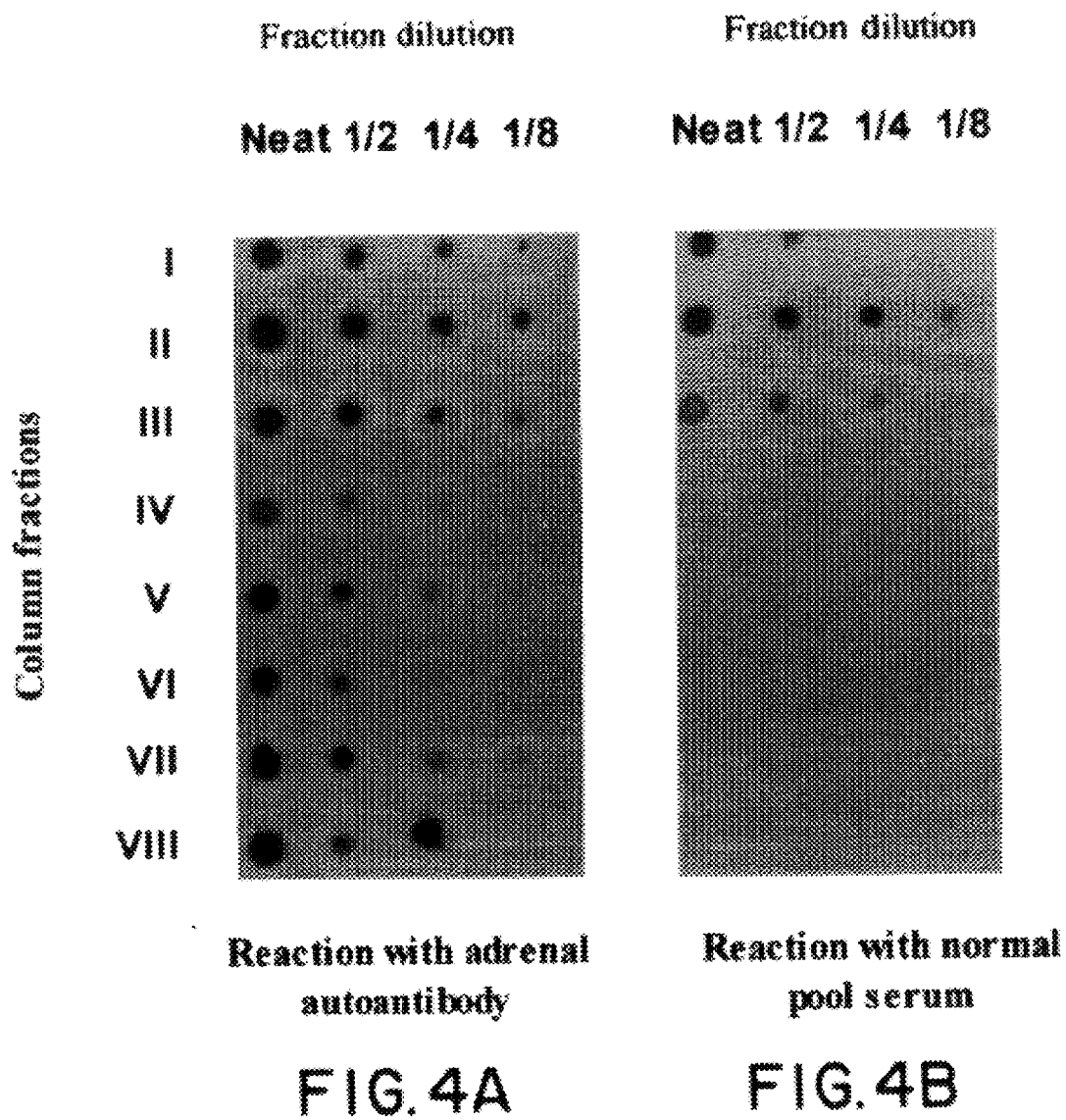
FIGS. 4A and 4B are dot blot assays of eluted column fractions contacted with (FIG. 4A) serum containing adrenal autoantibodies and (FIG. 4B) normal serum.
Figure 5:
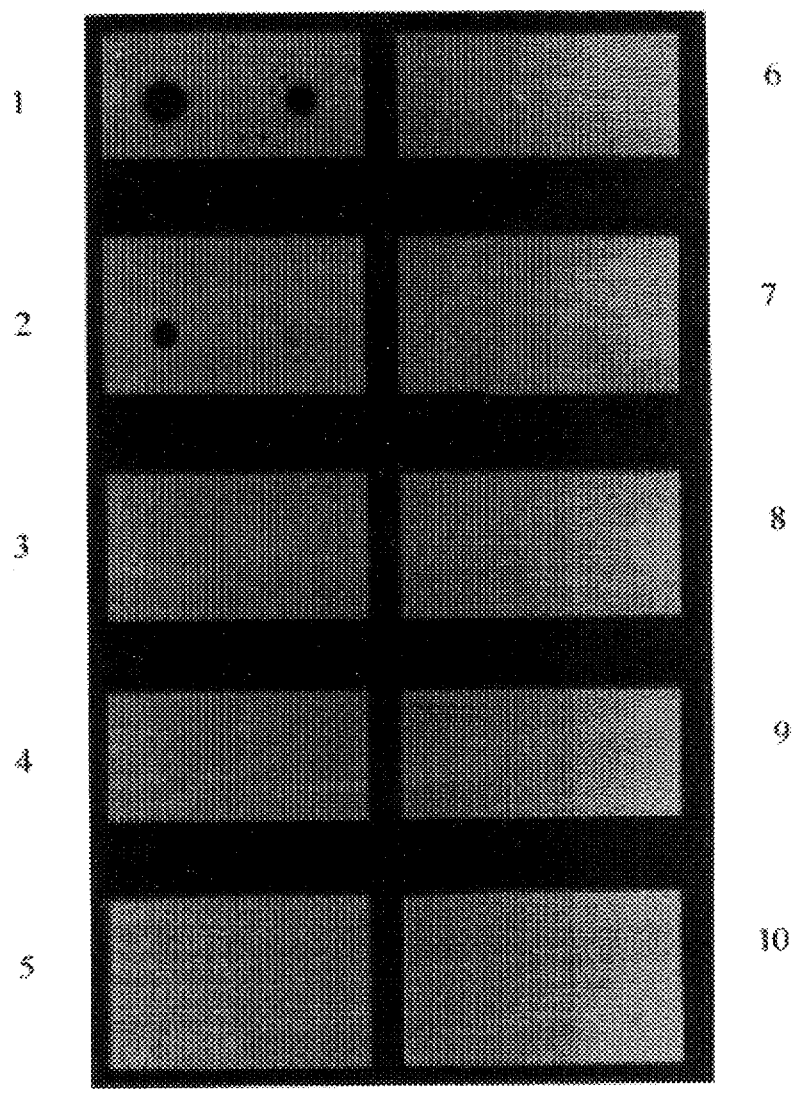
FIG. 5 shows a dot blot assay of eluted column fraction VI contacted with ten different serum samples.

As can be seen in FIG. 4B, dot blots of fractions I–III reacted strongly with normal pool serum and there was a weak interaction between fraction IV and normal pool serum. The Western blotting studies shown in FIG. 2B indicated that this effect of normal human serum was not due to an interaction with adrenal autoantigen. However, fractions I–IV were clearly unsuitable for use in analysis of serum adrenal autoantibodies. Fraction VI however did not show any interaction with normal pool serum in the dot blot system, suggesting that it could be used in a specific assay system for adrenal autoantibodies. Typical results using fraction VI in a dot-blot assay are shown in FIG. 5. The dot-blot assay whose results are shown in FIG. 5 was conducted using ten serum samples from different patients, as follows: samples 1 & 2: Addison's disease; sample 3: normal pool; samples 4 & 5: systemic lupus erythematoses; sample 6: Hashimoto's disease; samples 7 & 8: primary biliary cirrhosis; samples 9 & 10: Graves' disease.

Table 1 summarises data obtained with a group of Addison patients. Out of the 36 Addison sera analysed by dot blot assay, 26 (72%) were positive. Analysis of the sera by one or more of three different methods (immunofluorescence, immunoprecipitation or Western blot) confirmed the presence of adrenal autoantibodies in all 26 dot blot positive sera (Table 1). The 10 Addison sera negative by dot blot assay were also negative in the three other systems used to detect adrenal autoantibodies (Table 1). The 26 adrenal autoantibody positive patients had a high proportion of thyroid autoantibodies. In particular, TPO (thyroid peroxidase) autoantibodies in 22/26 (85%), Tg (thyroglobulin) autoantibodies in 17/26 (65%) and TRAb (thyroid stimulating hormone receptor antibodies) in 4/26 (15%). At least two of the TRAb positive patients (nos. 23 and 26) had well-documented histories of thyrotoxicosis. In contrast, the 10 Addison patients shown in Table 1 who were adrenal autoantibody negative had a similar proportion of thyroid autoantibodies as the normal population[18].

In dot blot assays of sera from 10 patients with Hashimoto's disease, 10 patients with Graves' disease, 5 patients with rheumatoid arthritis, 5 patients with systemic lupus erythematoses, 4 patients with primary biliary cirrhosis and 10 normal individuals, only one serum (from a patient with Graves' disease) was found to be positive. This positive Graves' serum was confirmed to have antibodies reactive with the 55,000 band on Western blot.

Our observations with the dot blot assay are in good agreement with previous studies of large numbers of sera using immunofluorescence[2,19–23]. For example, Nerup[20] and Blizzard[2] found that respectively 74% and 53% of patients with idiopathic Addison's disease had serum adrenal autoantibodies by immunofluorescene. Healthy normal donors rarely have adrenal autoantibodies detectable by immunofluorescence but most studies report adrenal autoantibodies in a few patients with non-adrenal autoimmune disease, including Graves' disease[20–23]. This is consistent with the detection of adrenal autoantibodies by dot blot in one Graves' serum.

TABLE 1

| | Adrenal Autoantibody Assays | | | | Thyroid Autoantibodies | | | |
|---|---|---|---|---|---|---|---|---|
| Addison Patient No: | Dot Blot | Western Blot | Immuno fluorescence | Immuno-precip. | TgAb U/mL | TPOAb U/mL | TRAb | Other Auto antibodies |
| 1  | + | ++++ | nt  | nt  | 0.6 | 30  | neg  |        |
| 2  | + | ++++ | nt  | nt  | 16  | 30  | neg  |        |
| 3  | + | +++  | nt  | nt  | 14.5| 30  | 45.5 |        |
| 4  | + | +++  | nt  | nt  | 6   | 30  | neg  |        |
| 5  | + | ++   | nt  | nt  | neg | 2.7 | neg  |        |
| 6  | + | +    | +   | +   | 30  | 30  | 91.9 | a, b, c |
| 7  | + | ++   | nt  | nt  | 1.2 | 21  | neg  |        |
| 8  | + | +    | nt  | nt  | neg | 2.0 | neg  |        |
| 9  | + | +    | nt  | nt  | neg | 26  | neg  |        |
| 10 | + | +    | nt  | nt  | 12.5| 17  | neg  |        |
| 11 | + | +++  | nt  | nt  | 7.5 | 1.9 | neg  |        |
| 12 | + | ++   | +   | +nt | 20  | 8.9 | neg  | a, c, d |
| 13 | + | ++   | nt  | nt  | neg | neg | neg  |        |
| 14 | + | +    | nt  | +   | 0.5 | 21  | neg  |        |
| 15 | + | nt   | +   | +   | neg | neg | neg  | c, e   |
| 16 | + | nt   | +   | +   | neg | neg | neg  |        |
| 17 | + | nt   | ++  | +   | 2.2 | 30  | neg  | b, c, g |
| 18 | + | +    | +   | +   | neg | neg | neg  | c      |
| 19 | + | +    | +   | +   | 1.7 | 21  | neg  | c      |
| 20 | + | +    | +   | +   | neg | 1.7 | neg  | c      |
| 21 | + | +    | +   | +   | neg | 25  | neg  | c      |
| 22 | + | +    | +   | +   | 16  | 34  | 18.3 |        |
| 23 | + | +    | +   | +   | 30  | 30  | neg  | d, e, f |
| 24 | + | +    | +   | +   | 8.4 | 12  | 6.8  |        |
| 25 | + | +    | +   | nt  | 30  | 30  | 47.6 | c      |
| 26 | + | +    | +   | nt  | 8.2 | 30  | neg  | c      |
| 27 | neg | nt | neg | neg | neg | neg | neg  |        |
| 28 | neg | nt | neg | neg | neg | neg | neg  |        |
| 29 | neg | nt | neg | neg | neg | neg | neg  |        |
| 30 | neg | nt | neg | neg | 0.4 | 8.6 | neg  | d      |
| 31 | neg | nt | neg | neg | neg | neg | neg  | c, d   |
| 32 | neg | nt | neg | neg | neg | 5.0 | neg  |        |
| 33 | neg | nt | neg | neg | neg | neg | neg  |        |
| 34 | neg | neg | neg | nt  | neg | neg | neg  |        |
| 35 | neg | neg | neg | nt  | neg | neg | neg  |        |
| 36 | neg | neg | neg | neg | neg | neg | neg  |        |

Key: a = antitubulin antibodies
b = anti-islet cell antibodies
c = anti-parietal cell antibodies
d = anti-nuclear antibodies
e = anti-mitochondrial antibodies
f = anti-desmin antibodies
g = anti-steroid producing cell antibodies
nt = not tested

EXAMPLE 6

Expression of 21-Hydroxylase in *Saccharomyces cerevisiae*

For expression in the yeast Saccharomyces cerevisiae, the plasmid yeast vector pYES 2.0 (obtained from Invitrogen) was used. The steroid 21-hydroxylase gene sequence in the plasmid vector pCD//pC21/3c[16] was obtained from the American Type Culture Collection, Rockville, USA (Deposit No 57421). The 21-hydroxylase gene sequence was subcloned as BamHI fragments (BamHI obtained from Northumbria Biologicals Ltd, Cramlington NE23 9HL, UK) into the cloning vector pTZ18 (obtained from Pharmacia).

After subcloning, further digestion was carried out using the enzyme SphI (Northumbria Biologicals Ltd, Cramlington NE23 9HL, UK) followed by NarI (Northumbria Biologicals Ltd, Cramlington NE23 9HL, UK) to obtain a large fragment comprising the entire coding region of the 21-hydroxylase gene apart from 41 base pairs at the 5' end.

The 21-hydroxylase gene so prepared was then ligated into the plasmid yeast vector pYES (cut with the enzymes BamHI and SphI) using a linker molecule consisting of parts of the STE2 gene (11 base pairs of non-coding sequence and 42 base pairs of coding sequence)[58]. The linker molecule was synthesised using an oligonucleotide synthesiser.

The 21-hydroxylase gene incorporated into the plasmid yeast vector in this way was then incorporated into yeast cells (Saccharomyces cerevisiae C13 ABYS 8B, Yeast Genetic Stock Center, Berkeley, Calif.) by electroporation (equipment obtained from Invitrogen) and the cells grown at 30° C. for 48 h on selective media (YND-glucose supplemented with amino acids except for uracil). The yeast cultures grown on selective media were used to inoculate larger expression cultures in YEP-glucose (2%) or YEP galactose (2%).

Yeast cells from 100 ml 48 h expression cultures were harvested at late-log phase, washed in 50 mM Tris-HCl pH 8.0 with addition of 1 mM phenyl-methyl-sulphonyl-fluoride (PMSF) and resuspended in 1 ml of 1% sodium deoxycholate in 50 mM Tris-HCl, pH 8.0 containing 1 mM PMSF. Acid treated beads (Sigma 450–500 um) were added and the cells broken by vortexing 10 times for 30 sec with 30 sec incubation on ice between such vortex period. After the removal of glass beads, the homogenates were centrifuged at 12,000×g for 2 min and the supernatants analysed on SDS-PAGE followed by Western blotting.

EXAMPLE 7

A Polypeptide Containing an Epitope to Adrenal Autoantibody

This Example describes the preparation of a polypeptide containing an epitope to adrenal autoantibody using the pYES2/human 21-OH construct with 21-OH controlled by the GAL1 promotor and including the yeast STE2 leader sequence. A series of truncations and deletions 3' from the leader sequence were made, expressed in yeast and tested for binding to rabbit antibody to 21-OH and adrenal autoantibody. In addition, protein expression and reaction with antibodies were analysed using the in vitro coupled reticulocyte lysate translation system.

Figure 8:
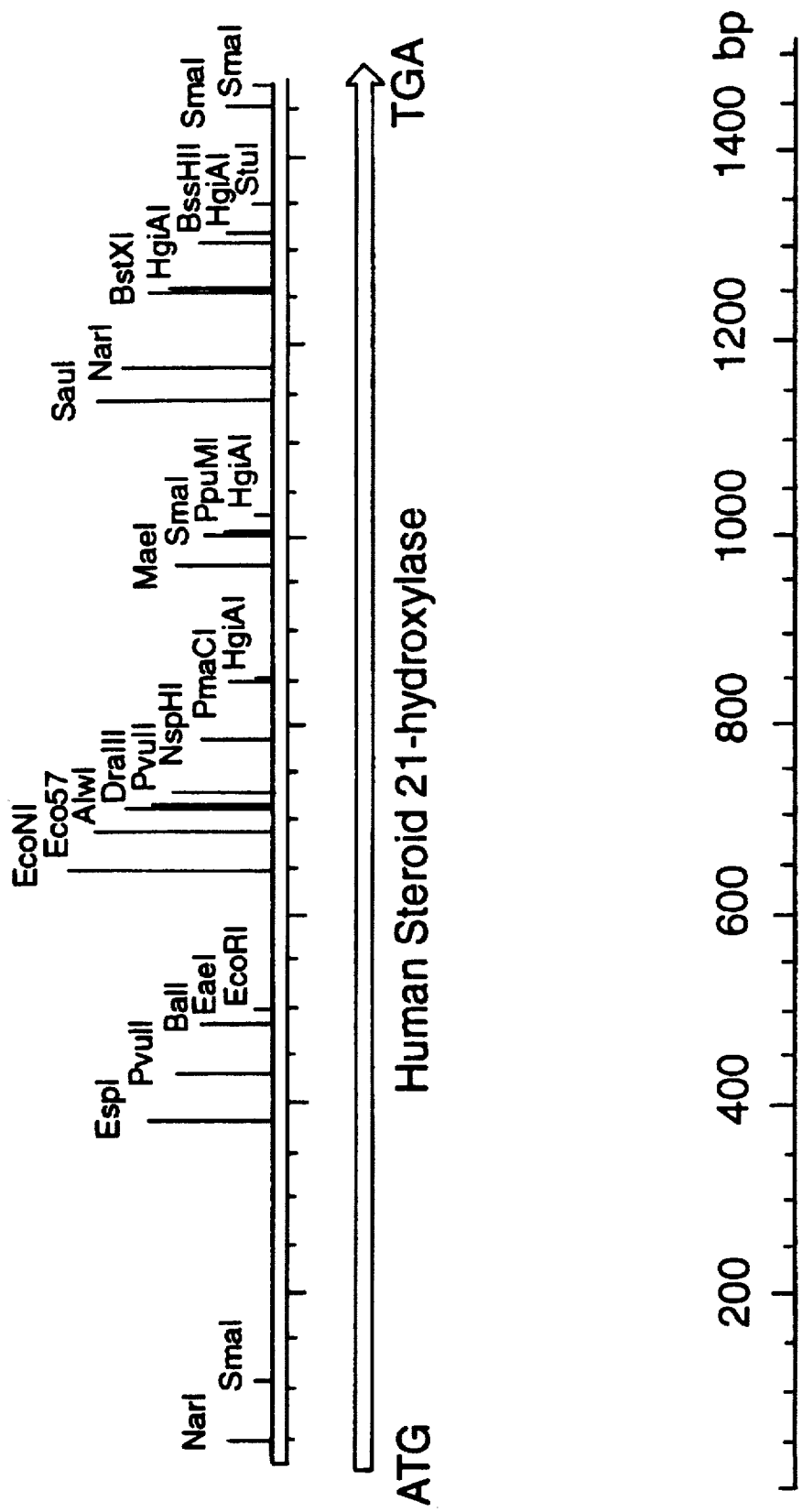
FIG. 8 is a schematic restriction enzyme map of the human steroid 21-hydroxylase gene.

To isolate modified 21-OH gene fragments, restriction sites within the gene sequence were used. The strategy involved isolation of suitable fragments from pYES2/21-OH which contains the full coding sequence of 21-OH (FIG. 8). The construction of pYES2/21-OH full length human 21-hydroxylase gene placed downstream of the GAL1 promotor in pYES2, (Invitrogen, distributed by British Biotechnology Products Ltd, Abingdon, UK) with the native signal peptide replaced by the leader sequence from the yeast STE2, gene is described in Example 6. In addition to the 21-hydroxylase coding sequence, pYES2/21-OH has 650 bp of non-coding sequence following the TGA stop codon which includes the polyadenylation signal and site.

The 21-OH full-length sequence with the STE2 leader sequence and the 650 bp non-coding sequence was cloned into the BamHI and SphI sites of the pYES2 multicloning site. The 5' end of the insert sequence was cloned into BamHI site and the 3' end into SphI site.

The vector pYES3 is a novel derivative of pYES2 constructed by cloning a specially-designed, unique linker into the EcoRI and SphI sites of the multiple cloning site of pYES2. The linker is shown in SEQ ID No. 2 of the accompanying sequence listing. The linker, prepared by annealing two chemically synthesised oligonucleotides, was designed to include PmaCI and SauI restriction sites for cloning and a series of TGA stop codons which ensured translation termination of all the truncated 21-hydroxylase genes.

21-OH gene fragments comprising a constant 5' end, but differing length of 21-OH coding sequence were isolated from pYES2/21-OH. This was accomplished by digestion with BamHI and either PmaCI, SauI or StuI, whose cleavage sites are indicated in sequence SEQ ID No. 1 of the sequence listing. A series of constructs was made by ligating these fragments into pYES3 (digested with BamHI and either PmaCI or SauI).

The two restriction sites included in the linker consisted of one "sticky end" site (SauI) and one "blunt end" site (PmaCI). These sites were used for cloning in the following way:—the 21-OH full-length sequence gene (containing BamHI site at the 5' end) after truncation at SauI site was cloned into the compatible sites in pYES3 (BamHI and SauI; the SauI site was provided by the incorporated linker). Similarly, the version of 21-OH which had been truncated at the PmaCI site was cloned into the BamHI and PmaCI sites of pYES3 (a compatible PmaCI site in the vector was provided by the linker sequence). Digestion of the 21-OH gene with StuI yielded the "blunt ended" gene sequence which could then be ligated into the "blunt end" site (PmaCI) of pYES3.

A construct with an internal PvuII deletion was prepared by cloning the 21-OH BamHI-PvuII and PvuII-SphI fragments excised from pYES2/21-OH into pYES3 cut with BamHI and SphI.

Figure 9:
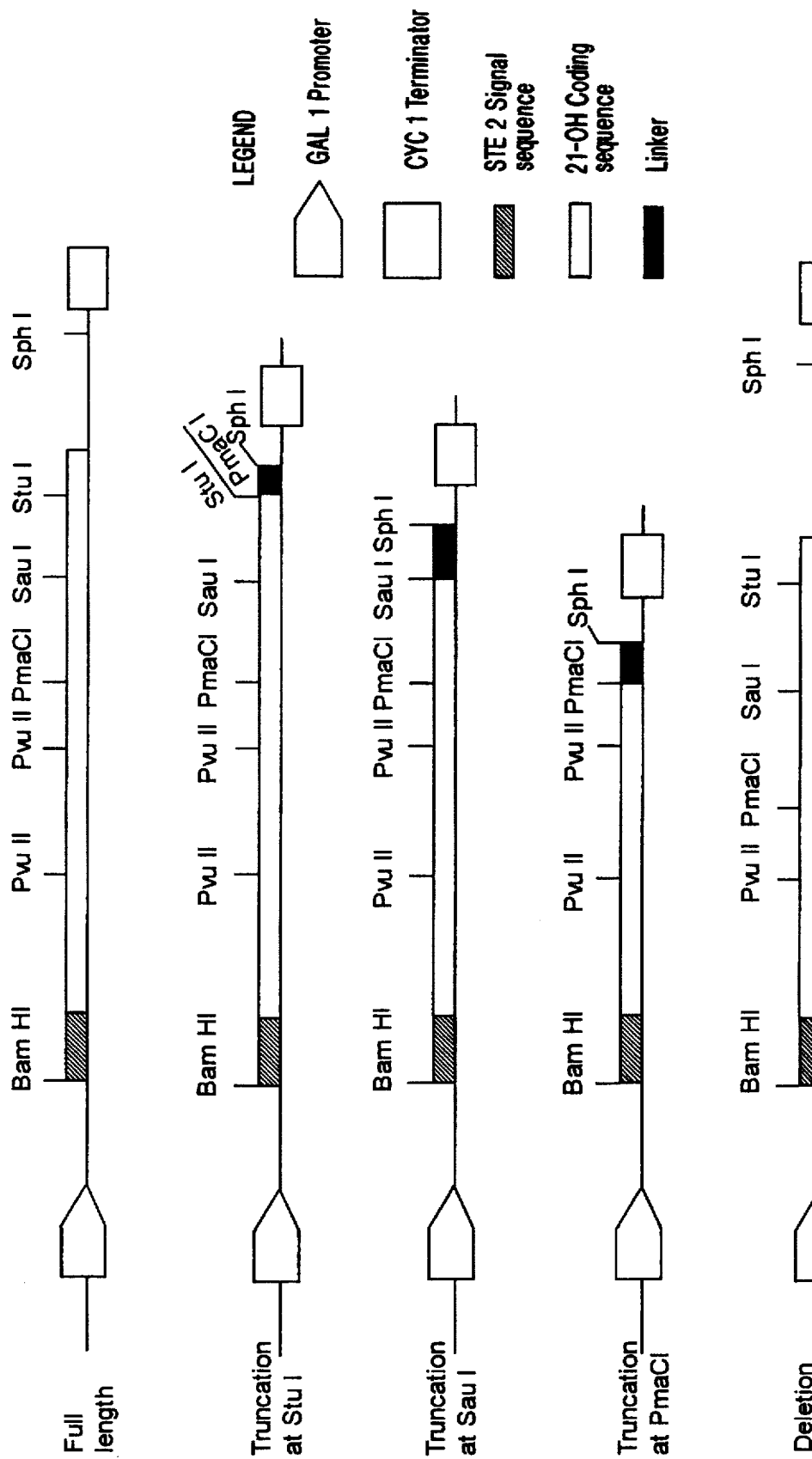
FIG. 9 is a schematic diagram of full-length, truncated and internally deleted steroid 21-hydroxylase coding sequence in vectors pYES2 and pYES3.

A schematic diagmM of full-length, truncated and internally deleted 21-OH constructs is shown in FIG. 9.

The cloning procedure involved a restriction digest of the pYES2/21-OH construct with the appropriate restriction endonucleases followed by analysis on 1% agarose gel. The 21-OH insert of the appropriate size was cut out of the agarose gel and purified using the Gene-clean reagents (Bio 101, supplied by Stratech Scientific). This insert was ligated into pYES3 cut with appropriate enzymes and transformed into E. Coli. In the case of PvuII deletion, the fragments BamHI-PvuII and PvuII-SphI were cut out from pYES2/21-OH, gene cleaned and ligated into PYES3 prepared by digestion with BamHI and SphI in a three-way ligation reaction.

Plasmid DNA was isolated from the transformed E.Coli and analysed by digestion with restriction endonucleases and electrophoresis on agarose gels. When the construct appeared to be correct, larger scale plasmid preparation was performed using Qiagen-100 kits (Qiagen, supplied by Hybaid Ltd). Pure preparations of plasmid DNA were checked by digestion with restriction enzymes in different combinations and when correct, used to transform the yeast, Saccharomyces cerevisiae, or used in an in vitro transcription/translation system (TnT coupled reticulocyte lysate system, Promega Corp., 2800 Woods Hollow Road, Madison, Wis. 53711-5399). The yeast transformants were grown under inducing conditions (YEP-galactose) as described in Example 6 and analysed on SDS-PAGE followed by Western blot.

Figure 10:
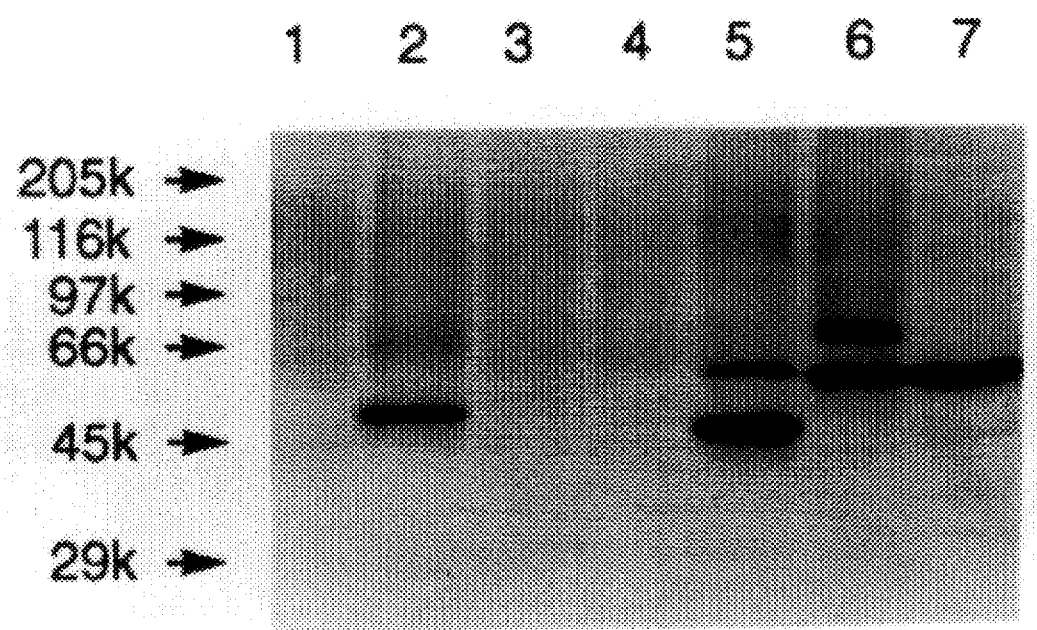
FIG. 10 shows a western blot of polypeptides produced in vitro and reacted with rabbit antibody to steroid 21-hydroxylase.
Figure 11:
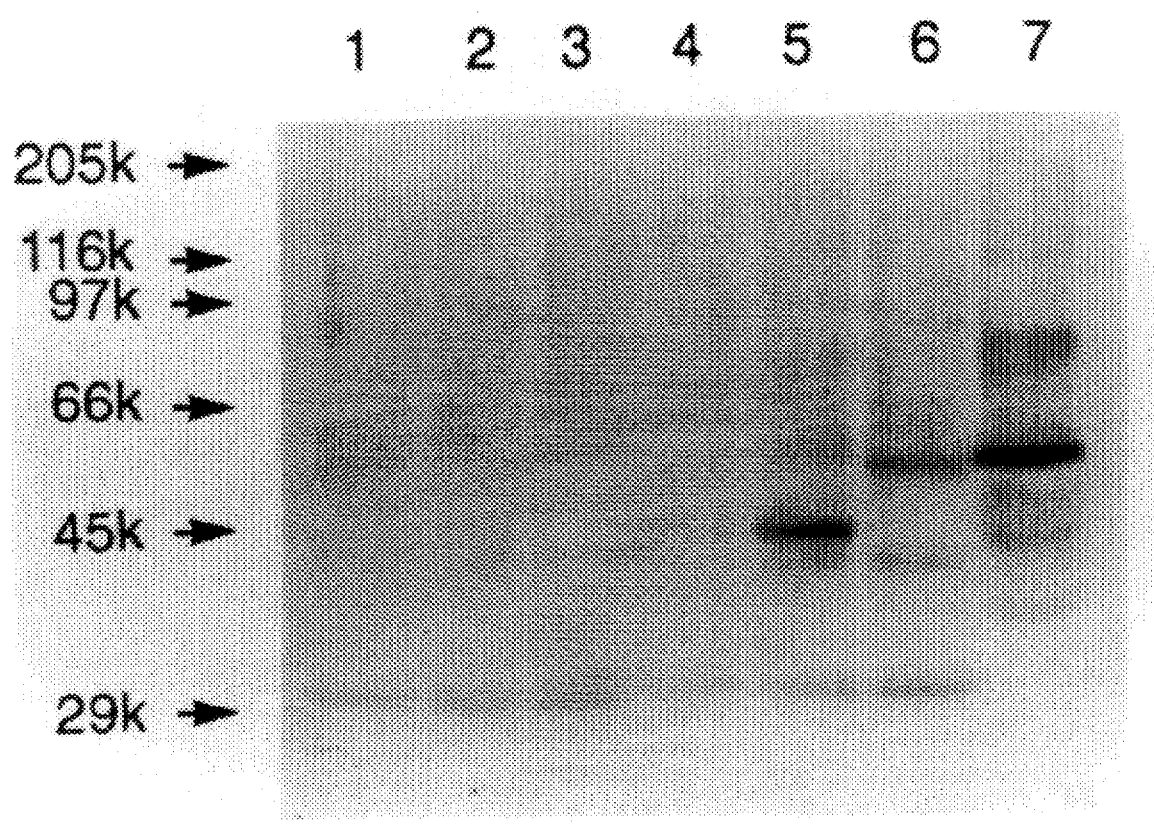
FIG. 11 shows a western blot of polypeptides produced in vitro and reacted with adrenal autoantibody.

Full length or modified proteins expressed in yeast or in TnT were analysed by western blotting using rabbit antibody and Addison sera. Addison pool serum and four individual sera from patients with high levels of adrenal autoantibody were used in these experiments. In addition, the recombinant proteins in TnT were labelled with $^{35}$S-methionine and analysed on SDS-PAGE followed by autoradiography. The analyses are shown in FIGS. 10 and 11. FIG. 10 is an analysis by SDS-PAGE and western blotting of polypeptides produced in vitro and reacted with rabbit antibody (Lane 1: reaction with in vitro transcription/translation of vector only; Lane 2: vector with 21-OH sequence truncated at StuI site; Lane 3: vector with 21-OH sequence truncated at SauI site; Lane 4: vector with 21-OH sequence truncated at PmaCI site; Lane 5: vector with 21-OH internal sequence deletion between PvuII and PvuII sites; Lane 6: vector with full length 21-OH sequence; Lane 7: full length 21-OH expressed in yeast). FIG. 11 is an analysis by SDS-PAGE and western blotting of proteins produced by in vitro transcription/translation and reacted with adrenal autoantibody (Lanes as FIG. 10).

The deletion between two PvuII sites had no effect on antibody and autoantibody binding to recombinant protein (FIGS. 10 and 11). The truncations at the SauI and PmaCI sites resulted in loss of the ability of the recombinant protein to bind rabbit antibody and autoantibody (FIGS. 10 and 11). Recombinant 21-OH after truncation at the StuI site reacted with rabbit antibody (FIG. 10), but not with adrenal autoantibody (FIG. 11).

These results are summarised in Table 2:

TABLE 2

| Modification | Length* | Mol. wt (SDS-PAGE) | Rabbit antibody binding Y | Rabbit antibody binding V | Auto-antibody binding Y | Auto-antibody binding V |
|---|---|---|---|---|---|---|
| None | AA 1–480 | 55K | + | + | + | + |
| Truncation at StuI site | AA 1–433 | 46K | + | + | (−) | (−) |
| Truncation at SauI site | AA 1–364 | 43K | (−) | (−) | (−) | (−) |
| Truncation at PmaCI site | AA 1–266 | 32K | (−) | (−) | (−) | (−) |
| Deletion PvuII—PvuII | AA 1–127 and 227–480 | 45K | + | + | + | + |

*The length is expressed in terms of the initialand final amino acids as numbered in SEQ ID No. 1.
Key: AA = amino acids, Y = expressed in yeast, V = expressed in vitro, + = reaction with antibody, (−) = no reaction with antibody.

Figure 12:
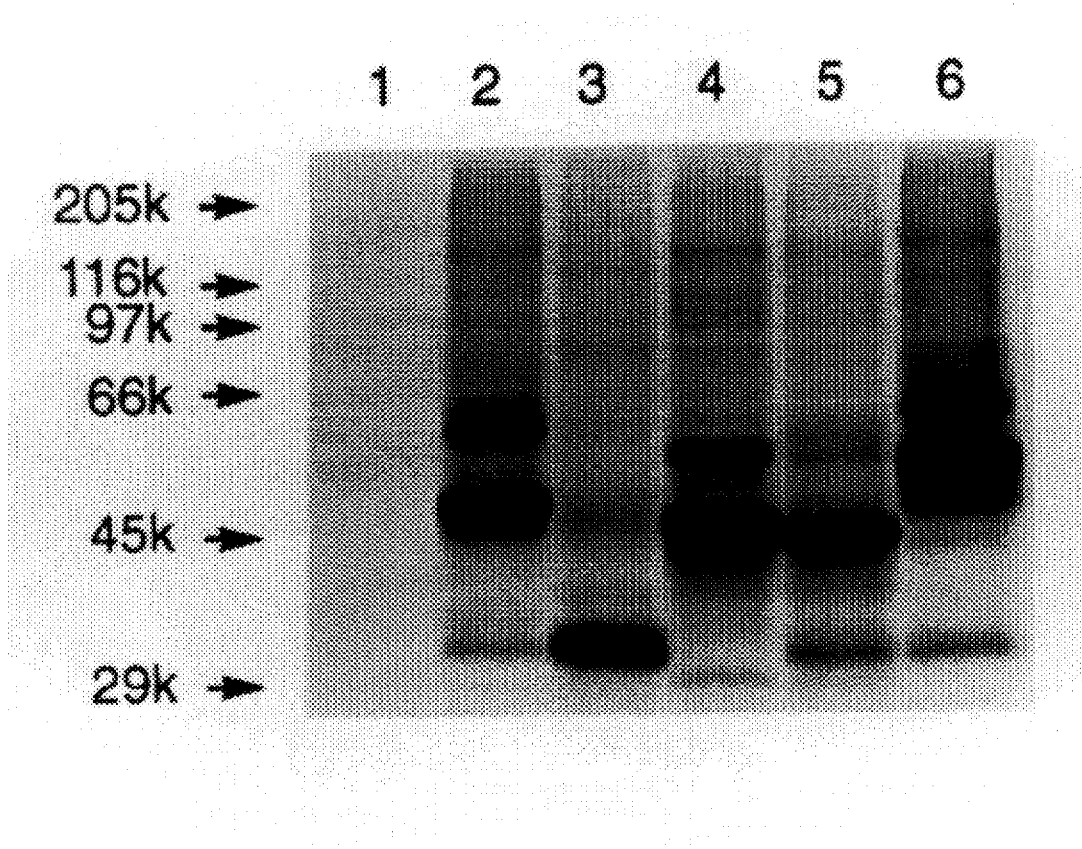
FIG. 12 shows an SDS-PAGE analysis followed by autoradiography of $^{35}$S-methionine labelled steroid 21-hydroxylase and polypeptides produced in vitro.

The introduced truncations and deletions did not affect the expression of the protein as shown in the in vitro translation experiments, the results of which appear in FIG. 12, which is an SDS-PAGE analysis followed by autoradiography of $^{35}$S-methionine labelled 21-OH and 21-OH fragments produced by the TnT in vitro transcription/translation system (Lanes as FIG. 10). There was a good agreement between the results obtained on western blot analysis of proteins expressed in the rabbit reticulocyte system and in yeast.

Analysis of autoantibody binding to recombinant 21-OH with mid-sequence deletions and 3' truncations indicated that the autoantibody binding site was located in a region at the carboxyl terminal end of the protein comprised in the region between residues 434 and 480. The deletion of large middle portions of the sequence did not affect autoantibody binding. This would suggest that the autoantibody epitope(s) on 21-OH are most probably linear which is consistent with previous observations. The number of autoantigenic epitopes situated on the fragment involved in autoantibody binding is almost certainly restricted.

The data indicate that the short fragment of 21-OH between amino acids 434 and 480 is important for adrenal autoantibody binding. Furthermore, derivatives (fragments) of 21-OH consisting of midsequence deletions such as the 396 AA preparations shown in Table 2 are suitable for use in adrenal autoantibody assays.

Bibliography

1. Anderson J R, Goudie R B, Gray K G, Timbury G C (1957) Lancet i:1123–1124
2. Blizzard R M, Kyle M (1963) J. Clin. Invest. 42:1653–1660.
3. Goudie R B, McDonald E, Anderson J R, Gray K (1968) Clin. exp. Immunol. 3:119–131.
4. Sotosiou F, Bottazzo G F, Doniach D (1980) Clin. exp. Immunol. 39:97–111.
5. Stechemesser E, Scherbaum W A, Grossmann T, Berg PA (1985) J. Immunol. Methods 80:67–76.
6. Kosowicz J, Gryczynska M, Bottazzo G F (1986) Clin. exp. Immunol.63:671–679.
7. Centeno E R, Shulman S (1973) Immunology 24:901–910
8. Bright G M and Singh I (1990) J Clin. Endocrinol. Metab. 70(1): 95–99
9. U.S. Pat. No. 4,720,454, White P C et al.
10. White P C, New M I, Dupont B (1986) Proc. Natl. Acad. Sci. USA 83:5111–5115
11. Furmaniak J, Talbot D, Reinwein D, Benker G, Creagh F M, Rees Smith B (1988) FEBS Letts 231:25–28.
12. Schardt C W, McLachlan S M, Matherson J, Rees Smith B (1982) J Immunol, Methods 55:155–168.
13. Kajita Y, Morgan D, Parkes A B, Rees Smith B (1985) FEBS Letts 187:334–338.
14. Bradford M (1976) Anal. Biochem. 72:248–254.
15. Kominami S, Ocho H, Kobayashi Y, Takemori S (1980) J Biol Chem. 255(8):3386–3394.
16. Bumpus J A, Dus K M (1982) J. Biol. Chem. 257(21):12696–12704.
17. Laemmli U K (1970) Nature 227:680–684.
18. Prentice L M, Phillips D I W, Sarsero D, Beever K, McLachlan S M, Rees Smith B (1990) Acta Endocrinol. 123:493–498.
19. Blizzard R M, Chee D, Davis W (1966) Clin. exp. Immunol. 1:119–128.
20. Nerup J (1974) Acta Endocrinol. (1974) 76:142–158.
21. Scherbaum W A, Berg P A (1982) Clin. Endocrinol. 16:345–352.
22. Betterle C, Zamchetta R, Trevisan A, Zanette F, Pedini B, Mantero F (4th Jun. 1983) Lancet:1238–1240.
23. Betterle C, Scalici C, Presotto, F, Pedini B, Moro L, Rigouo F, Mantero F (1988) J. Endocrinol 117:467–475.
24. Lather R F, Lecoq J P in Genetric Engineering, Academic Press 1983 (pp31–50).
25. Smith M, Gillam S in Genetic Engineering: Principles and Methods, Plenum Press (1981) 3:1–32.
26. Dalbadie-McFarland et al. (1982), Proc. Nafl. Acad. Sci. USA 79:6409–13.
27. Gillam et al. (1980) Gene 12:129–137.
28. Zoller M J, Smith M (1983) Meth. Enzymol. 100:468–500.
29. Kohler G, Milstein C (1975) Nature 256:495–497.
30. Kohler G, Milstein C (1976) Eur. J. Immunol. 6:511–519.
31. Kohler G, Milstein C (1976) Eur. J Immunol. 6:292.
32. Hammerling et al. in Monoclonal Antibodies and T-Cell Hybridomas, Elsevier, New York 1981 (pp 563–681).
33. Kennett R H, McKearn T J, Bechtol K B (editors), Monoclonal Antibodies, Plenum Press, New York (1980).
34. Melchers F, Potter M, Warner N (editors), Lymphocyte Hybridomas, Curr. Top. Microbiol. and Immunol, Springer-Verlag, Berlin 81:1–246(1978).
35. Vunakis H V, Langone J L (editors), Methods in Enzmology, Academic Press, Vols. 70, 73, 74, 84 and 92[Immunochemical Techniques parts A (1980), B (1981), C (1981), D (1982), E (1983)].
36. Janeway C (1989) Nature 341:482.
37. Acha-Orbea H et al. (1989) Ann. Rev. Immunol 7:371–405.
38. Kumar Vet al. (1989) Ann. Rev. Immunol 7:657–682.
39. Urban J Let al. (1989) Cell 54:577–592.
40. Wraith D C et al. (1989) Cell 57:709–715.
41. Wraith D C et al. (1989) Cell 59:247–255.
42. Urban J L et al. (1989) Cell 59:257–271.
43. Cohen I R (1986) Immunol. Rev. 94:5–21.
44. (1986)Prog. Immunol. VI:491–499.
45. (1988) Scientific Amer. 258:52–60.
46. (Feb. 15, 1989) Hosp. Prac. 57–64.
47. Cohen I R et al. (1988) Immunol. Today 9:332–335.
48. Vandenbark A A et al. (1989) Nature 341:541–544.
49. Howell M D et al. (1989) Science 246:668–671.
50. Sun D et al. (1988) Nature 332:843–845.
51. Sun D et al. (1988) Eur. J. Immunol. 18:1993–1999.
52. Green D et al. (1983) Ann. Rev. Immunol. 1:439.
53. Benacerraf B in The Biology of Immunologic Disease, H P Publishing Co Inc, New York 1983 (49–62).

54. Burns F J et al. (1989) J. Exp. Meal. 169:27.
55. Acha-Orbea H et al. (1989) Ann. Rev. Immunol. 7:371.
56. Hu M, Chung B (1990) Mol. Endocrinol 4:893–898

57. Craft J A, Jackson M R, Burcheil B (1987) Biochem. Soc. Trans. 15:708–709. King K, Dohlman H G, Thorner J, Caron M G, Lefkowitz R J (1990) Science 250:121–123

What is claimed is:

1. A method for diagnosing Addison's disease in a patient, comprising:

obtaining a sample containing antibodies from the patient; and detecting, in the sample, the presence or absence of antibodies which specifically bind a substantially pure microsomal protein comprising an epitope for adrenal autoantibody, having an observed molecular weight of approximately 55,000 as measured by gel electrophoresis and obtained by:

homogenizing mammalian adrenal glands, subjecting the homogenate to differential centrifugation to obtain a microsome fraction, suspending the microsome fraction in a phosphate buffer, centrifuging the suspension in the presence of sodium cholate to form a supernatant, adding polyethylene glycol and further sodium cholate to the supernatant and mixing the supernatant, centrifuging the thus mixed supernatant to form a pellet, resuspending the pellet in aqueous sodium cholate to form a suspension, dialyzing the suspension obtained by resuspending the pellet against aqueous sodium cholate to form a solubilized microsome preparation, and purifying the solubilized microsome preparation by column chromatography on a $C_8$ reversed phase column equilibrated with 50 mM phosphate buffer, pH 7.0, 20% glycerol, 0.1 mM EDTA, 0.1 mM DTT, and eluted with increasing concentration of detergent to obtain a column fraction corresponding to peak VI of FIG. 1 containing the microsomal protein;

wherein presence of said antibodies in said sample is indicative of Addison's disease in the patient.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1509 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Homo sapiens
        ( D ) DEVELOPMENTAL STAGE: foetus
        ( F ) TISSUE TYPE: adrenal gland ( i x ) FEATURE:
        ( A ) NAME/KEY: sig_peptide
        ( B ) LOCATION: 13..54

( i x ) FEATURE:
        ( A ) NAME/KEY: mat_peptide
        ( B ) LOCATION: 55..1494
        ( D ) OTHER INFORMATION: /product="steroid 21-hydroxylase"

( i x ) FEATURE:
        ( A ) NAME/KEY: CDS
        ( B ) LOCATION: 13..1494

( i x ) FEATURE:
        ( A ) NAME/KEY: misc_feature
        ( B ) LOCATION: (435  436)
        ( D ) OTHER INFORMATION: /standard_name="PvuII cleavage site"

( i x ) FEATURE:
        ( A ) NAME/KEY: misc_feature
        ( B ) LOCATION: (732  733)
        ( D ) OTHER INFORMATION: /standard_name="PvuII cleavage site"

( i x ) FEATURE:
        ( A ) NAME/KEY: misc_feature
        ( B ) LOCATION: (852  853)
        ( D ) OTHER INFORMATION: /standard_name="PmaCI cleavage site"

( i x ) FEATURE:
        ( A ) NAME/KEY: misc_feature
        ( B ) LOCATION: (1148  1149)
        ( D ) OTHER INFORMATION: /standard_name="SauI cleavage site"

( i x ) FEATURE:
        ( A ) NAME/KEY: misc_feature
        ( B ) LOCATION: (1354  1355)
        ( D ) OTHER INFORMATION: /standard_name="StuI cleavage site"

( i x ) FEATURE:
        ( A ) NAME/KEY: misc_feature
        ( B ) LOCATION: (53  54)
        ( D ) OTHER INFORMATION: /standard_name="NarI cleavage site"

( x i ) SEQUENCE DESCRIPTION: SEQ ID NO: 1:

| | | | | | | | | | | | | | | | | |
|---|---|---|---|---|---|---|---|---|---|---|---|---|---|---|---|---|
| GGGCGTCTCG | CC | ATG | CTG | CTC | CTG | GGC | CTG | CTG | CTG | CTG | CCC | CTG | CTG | | | 48 |
| | | Met | Leu | Leu | Leu | Gly | Leu | Leu | Leu | Leu | Pro | Leu | Leu | | | |
| | | -14 | | | -10 | | | | | | -5 | | | | | |

| GCT | GGC | GCC | CGC | CTG | CTG | TGG | AAC | TGG | TGG | AAG | CTC | CGG | AGC | CTC | CAC | 96 |
|---|---|---|---|---|---|---|---|---|---|---|---|---|---|---|---|---|
| Ala | Gly | Ala | Arg | Leu | Leu | Trp | Asn | Trp | Trp | Lys | Leu | Arg | Ser | Leu | His | |
| | | 1 | | | | 5 | | | | | | 10 | | | | |

| CTC | CCG | CCT | CTT | GCC | CCG | GGC | TTC | TTG | CAC | CTG | CTG | CAG | CCC | GAC | CTC | 144 |
|---|---|---|---|---|---|---|---|---|---|---|---|---|---|---|---|---|
| Leu | Pro | Pro | Leu | Ala | Pro | Gly | Phe | Leu | His | Leu | Leu | Gln | Pro | Asp | Leu | |
| 15 | | | | | 20 | | | | | 25 | | | | | 30 | |

| CCC | ATC | TAT | CTG | CTT | GGC | CTG | ACT | CAG | AAA | TTC | GGG | CCC | ATC | TAC | AGG | 192 |
|---|---|---|---|---|---|---|---|---|---|---|---|---|---|---|---|---|
| Pro | Ile | Tyr | Leu | Leu | Gly | Leu | Thr | Gln | Lys | Phe | Gly | Pro | Ile | Tyr | Arg | |
| | | | | 35 | | | | | 40 | | | | | 45 | | |

| CTC | CAC | CTT | GGG | CTG | CAA | GAT | GTG | GTG | GTG | CTG | AAC | TCC | AAG | AGG | ACC | 240 |
|---|---|---|---|---|---|---|---|---|---|---|---|---|---|---|---|---|
| Leu | His | Leu | Gly | Leu | Gln | Asp | Val | Val | Val | Leu | Asn | Ser | Lys | Arg | Thr | |
| | | | 50 | | | | | 55 | | | | | 60 | | | |

| ATT | GAG | GAA | GCC | ATG | GTC | AAA | AAG | TGG | GCA | GAC | TTT | GCT | GGC | AGA | CCT | 288 |
|---|---|---|---|---|---|---|---|---|---|---|---|---|---|---|---|---|
| Ile | Glu | Glu | Ala | Met | Val | Lys | Lys | Trp | Ala | Asp | Phe | Ala | Gly | Arg | Pro | |
| | 65 | | | | | 70 | | | | | 75 | | | | | |

| GAG | CCA | CTT | ACC | TAC | AAG | CTG | GTG | TCT | AAG | AAC | TAC | CCG | GAC | TTG | TCC | 336 |
|---|---|---|---|---|---|---|---|---|---|---|---|---|---|---|---|---|
| Glu | Pro | Leu | Thr | Tyr | Lys | Leu | Val | Ser | Lys | Asn | Tyr | Pro | Asp | Leu | Ser | |
| | 80 | | | | | 85 | | | | | 90 | | | | | |

| TTG | GGA | GAC | TAC | TCC | CTG | CTC | TGG | AAA | GCC | CAC | AAG | AAG | CTC | ACC | CGC | 384 |
|---|---|---|---|---|---|---|---|---|---|---|---|---|---|---|---|---|
| Leu | Gly | Asp | Tyr | Ser | Leu | Leu | Trp | Lys | Ala | His | Lys | Lys | Leu | Thr | Arg | |
| 95 | | | | | 100 | | | | | 105 | | | | | 110 | |

| TCA | GCC | CTG | CTG | CTG | GGC | ATC | CGT | GAC | TCC | ATG | GAG | CCA | GTG | GTG | GAG | 432 |
|---|---|---|---|---|---|---|---|---|---|---|---|---|---|---|---|---|
| Ser | Ala | Leu | Leu | Leu | Gly | Ile | Arg | Asp | Ser | Met | Glu | Pro | Val | Val | Glu | |
| | | | | 115 | | | | | 120 | | | | | 125 | | |

| CAG | CTG | ACC | CAG | GAG | TTC | TGT | GAG | CGC | ATG | AGA | GCC | CAG | CCC | GGC | ACC | 480 |
|---|---|---|---|---|---|---|---|---|---|---|---|---|---|---|---|---|
| Gln | Leu | Thr | Gln | Glu | Phe | Cys | Glu | Arg | Met | Arg | Ala | Gln | Pro | Gly | Thr | |
| | | | 130 | | | | | 135 | | | | | 140 | | | |

| CCT | GTG | GCC | ATT | GAG | GAG | GAA | TTC | TCT | CTC | CTC | ACC | TGC | AGC | ATC | ATC | 528 |
|---|---|---|---|---|---|---|---|---|---|---|---|---|---|---|---|---|
| Pro | Val | Ala | Ile | Glu | Glu | Glu | Phe | Ser | Leu | Leu | Thr | Cys | Ser | Ile | Ile | |
| | | 145 | | | | | 150 | | | | | 155 | | | | |

| TGT | TAC | CTC | ACC | TTC | GGA | GAC | AAG | ATC | AAG | GAC | GAC | AAC | TTA | ATG | CCT | 576 |
|---|---|---|---|---|---|---|---|---|---|---|---|---|---|---|---|---|
| Cys | Tyr | Leu | Thr | Phe | Gly | Asp | Lys | Ile | Lys | Asp | Asp | Asn | Leu | Met | Pro | |
| 160 | | | | | 165 | | | | | 170 | | | | | | |

| GCC | TAT | TAC | AAA | TGT | ATC | CAG | GAG | GTG | TTA | AAA | ACC | TGG | AGC | CAC | TGG | 624 |
|---|---|---|---|---|---|---|---|---|---|---|---|---|---|---|---|---|
| Ala | Tyr | Tyr | Lys | Cys | Ile | Gln | Glu | Val | Leu | Lys | Thr | Trp | Ser | His | Trp | |
| 175 | | | | | 180 | | | | | 185 | | | | | 190 | |

| TCC | ATC | CAA | ATT | GTG | GAC | GTG | ATT | CCC | TTT | CTC | AGG | TTC | TTC | CCC | AAT | 672 |
|---|---|---|---|---|---|---|---|---|---|---|---|---|---|---|---|---|
| Ser | Ile | Gln | Ile | Val | Asp | Val | Ile | Pro | Phe | Leu | Arg | Phe | Phe | Pro | Asn | |
| | | | | 195 | | | | | 200 | | | | | 205 | | |

| CCA | GGT | CTC | CGG | AGG | CTG | AAG | CAG | GCC | ATA | GAG | AAG | AGG | GAT | CAC | ATC | 720 |
|---|---|---|---|---|---|---|---|---|---|---|---|---|---|---|---|---|
| Pro | Gly | Leu | Arg | Arg | Leu | Lys | Gln | Ala | Ile | Glu | Lys | Arg | Asp | His | Ile | |
| | | | 210 | | | | | 215 | | | | | 220 | | | |

| GTG | GAG | ATG | CAG | CTG | AGG | CAG | CAC | AAG | GAG | AGC | CTC | GTG | GCA | GGC | CAG | 768 |
|---|---|---|---|---|---|---|---|---|---|---|---|---|---|---|---|---|
| Val | Glu | Met | Gln | Leu | Arg | Gln | His | Lys | Glu | Ser | Leu | Val | Ala | Gly | Gln | |
| | | 225 | | | | | 230 | | | | | 235 | | | | |

| TGG | AGG | GAC | ATG | ATG | GAC | TAC | ATG | CTC | CAA | GGG | GTG | GCG | CAG | CCG | AGC | 816 |
|---|---|---|---|---|---|---|---|---|---|---|---|---|---|---|---|---|
| Trp | Arg | Asp | Met | Met | Asp | Tyr | Met | Leu | Gln | Gly | Val | Ala | Gln | Pro | Ser | |
| | 240 | | | | | 245 | | | | | 250 | | | | | |

| ATG | GAA | GAG | GGC | TCT | GGA | CAG | CTC | CTG | GAA | GGG | CAC | GTG | CAC | ATG | GCT | 864 |
|---|---|---|---|---|---|---|---|---|---|---|---|---|---|---|---|---|
| Met | Glu | Glu | Gly | Ser | Gly | Gln | Leu | Leu | Glu | Gly | His | Val | His | Met | Ala | |
| 255 | | | | | 260 | | | | | 265 | | | | | 270 | |

| GCA | GTG | GAC | CTC | CTG | ATC | GGT | GGC | ACT | GAG | ACC | ACA | GCA | AAC | ACC | CTC | 912 |
|---|---|---|---|---|---|---|---|---|---|---|---|---|---|---|---|---|
| Ala | Val | Asp | Leu | Leu | Ile | Gly | Gly | Thr | Glu | Thr | Thr | Ala | Asn | Thr | Leu | |
| | | | | 275 | | | | | 280 | | | | | 285 | | |

| TCC | TGG | GCC | GTG | GTT | TTT | TTG | CTT | CAC | CAC | CCT | GAG | ATT | CAG | CAG | CGA | 960 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ser | Trp | Ala | Val | Val | Phe | Leu | Leu | His | His | Pro | Glu | Ile | Gln | Gln | Arg |      |
|     |     |     | 290 |     |     |     |     | 295 |     |     |     |     | 300 |     |     |      |
| CTG | CAG | GAG | GAG | CTA | GAC | CAC | GAA | CTG | GGC | CCT | GGT | GCC | TCC | AGC | TCC | 1008 |
| Leu | Gln | Glu | Glu | Leu | Asp | His | Glu | Leu | Gly | Pro | Gly | Ala | Ser | Ser | Ser |      |
|     |     | 305 |     |     |     |     | 310 |     |     |     |     | 315 |     |     |     |      |
| CGG | GTC | CCC | TAC | AAG | GAC | CGT | GCA | CGG | CTG | CCC | TTG | CTC | AAT | GCC | ACC | 1056 |
| Arg | Val | Pro | Tyr | Lys | Asp | Arg | Ala | Arg | Leu | Pro | Leu | Leu | Asn | Ala | Thr |      |
|     | 320 |     |     |     |     | 325 |     |     |     |     | 330 |     |     |     |     |      |
| ATC | GCC | GAG | GTG | CTG | CGC | CTG | CGG | CCC | GTT | GTG | CCC | TTA | GCC | TTG | CCC | 1104 |
| Ile | Ala | Glu | Val | Leu | Arg | Leu | Arg | Pro | Val | Val | Pro | Leu | Ala | Leu | Pro |      |
| 335 |     |     |     |     | 340 |     |     |     |     | 345 |     |     |     |     | 350 |      |
| CAC | CGC | ACC | ACA | CGG | CCC | AGC | AGC | ATC | TCT | GGC | TAC | GAC | ATC | CCT | GAG | 1152 |
| His | Arg | Thr | Thr | Arg | Pro | Ser | Ser | Ile | Ser | Gly | Tyr | Asp | Ile | Pro | Glu |      |
|     |     |     |     | 355 |     |     |     |     | 360 |     |     |     |     | 365 |     |      |
| GGC | ACA | GTC | ATC | ATT | CCG | AAC | CTC | CAA | GGC | GCC | CAC | CTG | GAT | GAG | ACG | 1200 |
| Gly | Thr | Val | Ile | Ile | Pro | Asn | Leu | Gln | Gly | Ala | His | Leu | Asp | Glu | Thr |      |
|     |     |     | 370 |     |     |     |     | 375 |     |     |     |     | 380 |     |     |      |
| GTC | TGG | GAG | AGG | CCA | CAT | GAG | TTC | TGG | CCT | GAT | CGC | TTC | CTG | GAG | CCA | 1248 |
| Val | Trp | Glu | Arg | Pro | His | Glu | Phe | Trp | Pro | Asp | Arg | Phe | Leu | Glu | Pro |      |
|     |     | 385 |     |     |     |     | 390 |     |     |     |     | 395 |     |     |     |      |
| GGC | AAG | AAC | TCC | AGA | GCT | CTG | GCC | TTC | GGC | TGC | GGT | GCC | CGC | GTG | TGC | 1296 |
| Gly | Lys | Asn | Ser | Arg | Ala | Leu | Ala | Phe | Gly | Cys | Gly | Ala | Arg | Val | Cys |      |
|     | 400 |     |     |     |     | 405 |     |     |     |     | 410 |     |     |     |     |      |
| CTG | GGC | GAG | CCG | TTG | GCG | CGC | CTG | GAG | CTC | TTC | GTG | GTG | CTG | ACC | CGA | 1344 |
| Leu | Gly | Glu | Pro | Leu | Ala | Arg | Leu | Glu | Leu | Phe | Val | Val | Leu | Thr | Arg |      |
| 415 |     |     |     |     | 420 |     |     |     |     | 425 |     |     |     |     | 430 |      |
| CTG | CTG | CAG | GCC | TTC | ACG | CTG | CTG | CCC | TCC | GGG | GAC | GCC | CTG | CCC | TCC | 1392 |
| Leu | Leu | Gln | Ala | Phe | Thr | Leu | Leu | Pro | Ser | Gly | Asp | Ala | Leu | Pro | Ser |      |
|     |     |     |     | 435 |     |     |     |     | 440 |     |     |     |     | 445 |     |      |
| CTG | CAG | CCC | CTG | CCC | CAC | TGC | AGT | GTC | ATC | CTC | AAG | ATG | CAG | CCT | TTC | 1440 |
| Leu | Gln | Pro | Leu | Pro | His | Cys | Ser | Val | Ile | Leu | Lys | Met | Gln | Pro | Phe |      |
|     |     |     | 450 |     |     |     |     | 455 |     |     |     |     | 460 |     |     |      |
| CAA | GTG | CGG | CTG | CAG | CCC | CGG | GGG | ATG | GGG | GCC | CAC | AGC | CCG | GGC | CAG | 1488 |
| Gln | Val | Arg | Leu | Gln | Pro | Arg | Gly | Met | Gly | Ala | His | Ser | Pro | Gly | Gln |      |
|     |     | 465 |     |     |     |     | 470 |     |     |     |     | 475 |     |     |     |      |
| AAC | CAG | TGATGGGGCA | GGACC |     |     |     |     |     |     |     |     |     |     |     |     | 1509 |
| Asn | Gln |     |     |     |     |     |     |     |     |     |     |     |     |     |     |      |
|     | 480 |     |     |     |     |     |     |     |     |     |     |     |     |     |     |      |

( 2 ) INFORMATION FOR SEQ ID NO: 2:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: misc_feature
        ( B ) LOCATION: 1..4
        ( D ) OTHER INFORMATION: /standard_name="EcoRI restriction
            end"

( i x ) FEATURE:
        ( A ) NAME/KEY: misc_feature
        ( B ) LOCATION: (7 8)
        ( D ) OTHER INFORMATION: /standard_name="SauI cleavage
            site"

( i x ) FEATURE:
        ( A ) NAME/KEY: misc_feature
        ( B ) LOCATION: (16 17)
        ( D ) OTHER INFORMATION: /standard_name="PmaCI cleavage site"

(ix) FEATURE:
    (A) NAME/KEY: misc_feature
    (B) LOCATION: 31..33
    (D) OTHER INFORMATION: /standard_name="SphI restriction end"

(ix) FEATURE:
    (A) NAME/KEY: misc_feature
    (B) LOCATION: 8..10
    (D) OTHER INFORMATION: /standard_name="Stop codon"

(ix) FEATURE:
    (A) NAME/KEY: misc_feature
    (B) LOCATION: 18..20
    (D) OTHER INFORMATION: /standard_name="Stop codon"

(ix) FEATURE:
    (A) NAME/KEY: misc_feature
    (B) LOCATION: 22..24
    (D) OTHER INFORMATION: /standard_name="Stop codon"

(ix) FEATURE:
    (A) NAME/KEY: misc_feature
    (B) LOCATION: 26..28
    (D) OTHER INFORMATION: /standard_name="Stop codon"

(xi) SEQUENCE DESCRIPTION: SEQ ID NO: 2:

AATTCCCTGA GGCCACGTGA CTGACTGAGC ATG     33